US012322091B2

United States Patent
Conjeti et al.

(10) Patent No.: US 12,322,091 B2
(45) Date of Patent: Jun. 3, 2025

(54) METHOD FOR PROVIDING AT LEAST ONE METADATA ATTRIBUTE ASSOCIATED WITH A MEDICAL IMAGE

(71) Applicant: Siemens Healthcare GmbH, Erlangen (DE)

(72) Inventors: Sailesh Conjeti, Erlangen (DE); Alexis Laugerette, Erlangen (DE); Christian Huemmer, Lichtenfels (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 556 days.

(21) Appl. No.: 17/671,950

(22) Filed: Feb. 15, 2022

(65) Prior Publication Data
US 2022/0277444 A1 Sep. 1, 2022

(30) Foreign Application Priority Data
Mar. 1, 2021 (DE) ...................... 10 2021 201 912.9

(51) Int. Cl.
*G06T 7/12* (2017.01)
*G06T 7/00* (2017.01)
(52) U.S. Cl.
CPC .. *G06T 7/0012* (2013.01); *G06T 2207/20081* (2013.01); *G06T 2207/20084* (2013.01)
(58) Field of Classification Search
CPC ......... G06T 7/0012; G06T 2207/20081; G06T 2207/20084

(Continued)

(56) References Cited

U.S. PATENT DOCUMENTS 8,200,505 B2 6/2012 Kostrzewa et al.
8,634,673 B1 1/2014 McDougal et al.
(Continued)

FOREIGN PATENT DOCUMENTS

| CN | 101084501 A | 12/2007 |
|---|---|---|
| EP | 3451344 A1 | 3/2019 |
| WO | WO 2017024787 A1 | 2/2017 |

OTHER PUBLICATIONS

Swada, Azusa et al: "Overcoming Labeling Ability for Latent Positives:Automatic Label Correction along Data Series"; NEC Corpolation, Kanagawa, Japan; In Proceedings of the 8th International Conference on Pattern Recognition Applications and Methods (ICPRAM 2019); pp. 406-413, Year: 2019; DOI: 10.5220/0007341704060413.

(Continued)

*Primary Examiner* — Michael R Neff
(74) *Attorney, Agent, or Firm* — Harness, Dickey & Pierce, P.L.C.

(57) ABSTRACT

A computer-implemented method is for providing at least one first metadata attribute associated with a medical image. The method includes receiving the medical image and the at least one first metadata attribute. Therein the at least one first metadata attribute includes an attribute tag and a provisional attribute value. Furthermore, the method includes applying a first trained function to the medical image to determine an image-based attribute value. Furthermore, the method includes determining a final attribute value based on the provisional attribute value and the image-based attribute value. Furthermore, the method includes providing the at least one first metadata attribute. Therein the at least one first metadata attribute includes the attribute tag and the final attribute value.

20 Claims, 10 Drawing Sheets

(58) Field of Classification Search
USPC .......................................................... 382/128
See application file for complete search history.

(56) References Cited

U.S. PATENT DOCUMENTS

| | | |
|---|---|---|
| 10,140,553 B1 | 11/2018 | Vasisht et al. |
| 2006/0115135 A1 | 6/2006 | Dehmeshki et al. |
| 2014/0247992 A1 | 9/2014 | Lin et al. |
| 2018/0012110 A1 | 1/2018 | Souche et al. |
| 2020/0203002 A1 | 6/2020 | Amthor et al. |
| 2020/0364858 A1 | 11/2020 | Kaethner et al. |
| 2020/0394814 A1 | 12/2020 | Schulter |
| 2021/0174503 A1* | 6/2021 | Trautwein .............. G16H 50/70 |

OTHER PUBLICATIONS

Signe Anthon et al.; "Socially optimal procurement with tight budgets and rationing"; Journal of Public Economics; vol. 91; No. 07; pp. 1625-1642; Aug. 31, 2007;.

Wang Xiaomin et al.; "Establishment of a Biomedical Image Information Database"; Chinese Journal of Stereology and Image Analysis; No. 03; Mar. 9, 2008; pp. 64-67.

Zhou Jie et al.; "MOAB Classification Coding Scheme for Medical Image Retrieval"; Journal of Image and Graphics; No. 02; pp. 31-35; Feb. 25, 2004.

* cited by examiner

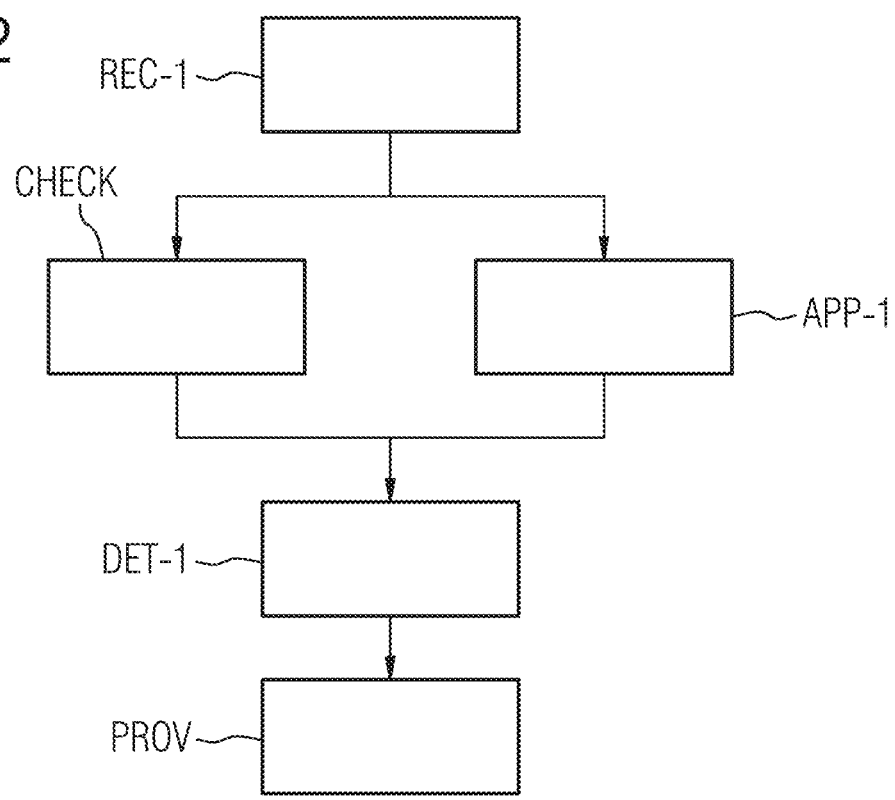
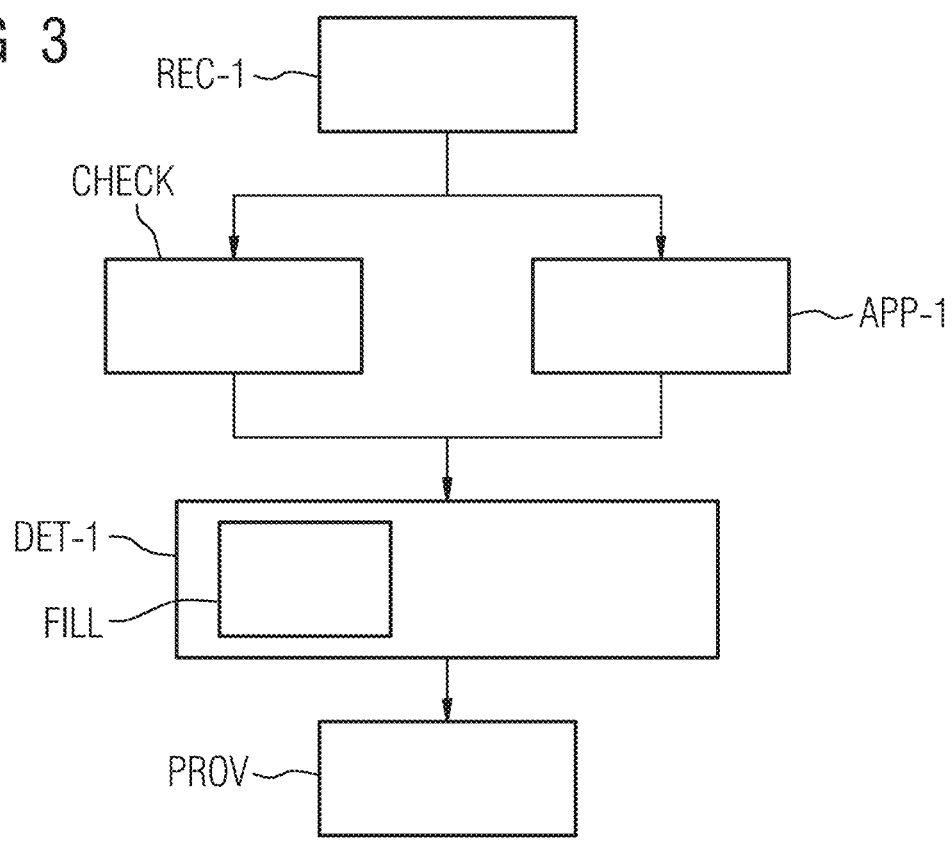

METHOD FOR PROVIDING AT LEAST ONE METADATA ATTRIBUTE ASSOCIATED WITH A MEDICAL IMAGE

PRIORITY STATEMENT

The present application hereby claims priority under 35 U.S.C. § 119 to German patent application number DE 102021201912.9 filed Mar. 1, 2021, the entire contents of which are hereby incorporated herein by reference.

FIELD

Example embodiments of the invention generally relate to a method and a device for providing at least one metadata attribute associated with a medical image.

BACKGROUND

Medical images of an examination object can be acquired during an examination or during a diagnostic process. The examination object can at least comprise a part respectively an organ of a human being, an animal and/or an object. It is known that at least one metadata attribute is associated with a medical image. The metadata attribute is designed for describing for example to which examination, which diagnostic process, which examination object and/or which part of the examination objects the associated medical image is related to. Alternatively, or additionally, the metadata attribute can precise at least one examination parameter which has been used for acquiring the medical image. A metadata attribute usually comprises an attribute tag and an attribute value. The attribute tag describes what the metadata attribute refers to. The attribute value provides the concrete value of the metadata attribute. The attribute value is usually determined automatically and/or manually. For example, the metadata attribute can be filled in manually by a medical doctor or a medical assistant or a technologist during the imaging process. Filling in the metadata attribute means that the attribute value is filled in by a string or a digit (e.g. an integer, a float etc.). Alternatively or additionally, the metadata attribute can be determined automatically. For example, the metadata attribute can be filled in based on a protocol which has been used for acquiring the associated medical image.

In some cases, the metadata attribute can be filled in incorrectly and/or incomplete. For example, a protocol for imaging a hand is used for imaging a foot. The attribute value of the metadata attribute with the attribute tag 'Body part examined' is automatically filled by the string 'foot'. As an alternative example the medical doctor or the medical assistant forgot to fill in a metadata attribute. Alternatively or additionally, the metadata attribute might be filled in with an abbreviation or an individual expression instead of a standardized label when it is filled in manually.

SUMMARY

Because of this, the inventors discovered that it might be impossible to compare different medical images in a database based on the metadata attributes. For example, querying for all medical images which are associated to a metadata attribute with an attribute tag 'Body part examined' and an attribute value 'foot' might result according to the example from above to a plurality of medical images wherein at least one comprises an image of a hand. Furthermore, if the attribute value is filled manually, it might not be possible to query for a specific group of medical images based on the attribute values, because the attribute values are not standardized.

Furthermore, the inventors discovered that an application which is applied on the medical image might need an information based on the correctly filled attribute value of a metadata attribute. For example, an application which provides a diagnosis or makes automated measurements based on the medical image might need an information about the examination object. This information should be provided by the corresponding correct and/or standardized attribute value.

Hence, the inventors discovered that empty, incorrect and/or not standardized attribute values can cause problems concerning the further processing of the medical image based on the at least one metadata attribute. Hence, the metadata attributes and their corresponding attribute values should be unified.

At least one embodiment of the present invention provides a method unifying a metadata attribute associated to a medical image.

Embodiments are directed to a method, a unifying system, a computer program product and a computer-readable storage medium. Advantageous features and further developments are listed in the claims and in the following specification.

In the following, the solution according to the embodiments is described with respect to the unifying systems as well as with respect to the methods. Features, advantages or alternative embodiments herein can be assigned to the other claimed objects and vice versa. In other words, claims for the unifying systems can be improved with features described or claimed in the context of the methods. In this case, the functional features of the method are embodied by objective units of the unifying system.

In a first embodiment, the invention relates to a computer-implemented method for providing at least one first metadata attribute associated with a medical image. The method comprises a step of receiving the medical image and the at least one first metadata attribute, wherein the at least one first metadata attribute comprises an attribute tag and a provisional attribute value. In a further step, the method comprises applying a first trained function to the medical image so as to determine an image-based attribute value. In a further step, the method comprises determining a final attribute value based on the provisional attribute value and the image-based attribute value. In a further step, the method comprises providing the at least one first metadata attribute, wherein the at least one first metadata attribute comprises the attribute tag and the final attribute value.

In a second embodiment the invention relates to a unifying system for providing at least one first metadata attribute associated with a medical image. The unifying system comprises an interface and a computation unit. Therein the interface is configured for receiving the medical image and the at least one first metadata attribute. Therein the at least one first metadata attribute comprises an attribute tag and a provisional attribute value. Therein the computation unit is configured for applying a first trained function to the medical image so as to determine an image-based attribute value. Therein the computation unit is configured for determining a final attribute value based on the provisional attribute value and the image-based attribute value. Therein the interface is configured for providing the at least one metadata attribute. Therein the at least one metadata attribute comprises the attribute tag and the final attribute vale.

In a third embodiment the invention relates to a computer program product with a computer program and a computer-readable medium. A mainly software-based implementation has the advantage that even previously used unifying systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a fourth embodiment the invention relates to a computer-readable storage medium comprising program elements which are readable and executable by a unifying system, to execute the claimed method and its embodiments, when the program elements are executed by the unifying system.

At least one embodiment is directed to a computer-implemented method for providing at least one first metadata attribute associated with a medical image, the method comprising:
receiving the medical image and the at least one first metadata attribute, the at least one first metadata attribute including an attribute tag and a provisional attribute value;
applying a first trained function to the medical image to determine an image-based attribute value;
determining a final attribute value based on the provisional attribute value and the image-based attribute value; and
providing the at least one first metadata attribute, the at least one first metadata attribute including the attribute tag and the final attribute value.

At least one embodiment is directed to a unifying system for providing at least one metadata attribute associated with a medical image,
comprising:
an interface, configured to receive the medical image and the at least one metadata attribute, the at least one metadata attribute including an attribute tag and a provisional attribute value; and
a computation unit, configured to
apply a first trained function to the medical image to determine an image-based attribute value,
determine a final attribute value based on the provisional attribute value and the image-based attribute value,
wherein the interface is further configured to provide the at least one metadata attribute, and
wherein the at least one metadata attribute includes the attribute tag and the final attribute value.

At least one embodiment is directed to a non-transitory computer program product storing program elements, directly loadable into a memory unit of a unifying system, to induce the unifying system to execute the method of claim 1, when the program elements are executed by the unifying system.

At least one embodiment is directed to a non-transitory computer-readable storage medium storing program elements which are readable and executable by a unifying system, to execute the method of claim 1 when the program elements are executed by the unifying system.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

DETAILED DESCRIPTION OF THE EXAMPLE EMBODIMENTS

Figure 1:
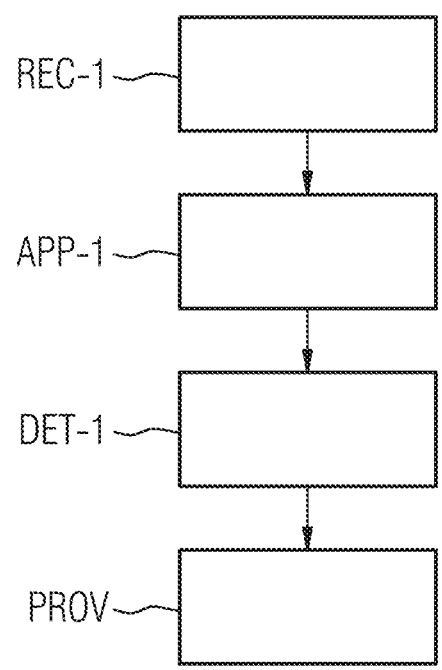
FIG. 1 displays a schematic flow chart of a first embodiment of the method for providing at least one first metadata attribute associated with a medical image, FIG. 2 displays a schematic flow chart of a second embodiment of the method for providing at least one first metadata attribute associated with a medical image, FIG. 3 displays a schematic flow chart of a third embodiment of the method for providing at least one first metadata attribute associated with a medical image, FIG. 4 displays a schematic flow chart of a fourth embodiment of the method for providing at least one first metadata attribute associated with a medical image, FIG. 5 displays a schematic flow chart of a fifth embodiment of the method for providing at least one first metadata attribute associated with a medical image, FIG. 6 displays a schematic flow chart of a sixth embodiment of the method for providing at least one first metadata attribute associated with a medical image, FIG. 7 displays a schematic flow chart of a seventh embodiment of the method for providing at least one first metadata attribute associated with a medical image, FIG. 8 displays a schematic flow chart of an eighth embodiment of the method for providing at least one first metadata attribute associated with a medical image, FIG. 9 displays a schematic flow chart of a ninth embodiment of the method for providing at least one first metadata attribute associated with a medical image, FIG. 10 displays a schematic flow chart of a tenth embodiment of the method for providing at least one first metadata attribute associated with a medical image, FIG. 11 displays a schematic flow chart of a eleventh embodiment of the method for providing at least one first metadata attribute associated with a medical image, FIG. 12 displays a unifying system for providing at least one first metadata attribute associated with a medical image, FIG. 13 displays a training system for providing a first trained function.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices.

The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device may also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the invention relates to a computer-implemented method for providing at least one first metadata attribute associated with a medical image. The method comprises a step of receiving the medical image and the at least one first metadata attribute, wherein the at least one first metadata attribute comprises an attribute tag and a provisional attribute value. In a further step, the method comprises applying a first trained function to the medical image so as to determine an image-based attribute value. In a further step, the method comprises determining a final attribute value based on the provisional attribute value and the image-based attribute value. In a further step, the method comprises providing the at least one first metadata attribute, wherein the at least one first metadata attribute comprises the attribute tag and the final attribute value.

The medical image can in particular be acquired by a medical imaging system. The medical imaging system can for example be one out of an X-ray system, a Computed-Tomography (CT) system, a Magnetic-Resonance-Imaging (MRI) system, an angiography system, a C-arm system, an ultrasonic system, a Positron-Emission-Tomography (PET) system, a Single-Photon-Emission-Computed-Tomography (SPECT) system. The medical image can in particular be a pixelimage or a voxelimage. With other words, the medical image can comprise a pixelmatrix or a voxelmatrix, wherein the pixelmatrix respectively the voxelmatrix comprises a plurality of pixels respectively of voxels. Hence, the medical image can be a two-dimensional or a three-dimensional medical image. Alternatively, the medical image can be a four-dimensional medical image. A four-dimensional medical image can comprise a time-series of three-dimensional medical images. Such a four-dimensional medical image can be for example a Cine-Magnetic-Resonance-Image. Alternatively, a four-dimensional medical image can for example comprise a cardiac gated Computed-Tomography scan.

The medical image can depict an examination object. The examination object can be at least a part or an organ of a human being or an animal or a subject.

The medical image is associated to at least one first metadata attribute. In particular, the medical image can be associated to a plurality of metadata attributes, wherein the at least one first metadata attribute is one of the plurality of metadata attributes. The at least one first metadata attribute describes for example what is depicted by the medical image, by which medical imaging system the medical image is acquired and/or which parameters are used for acquiring the medical image. In particular, the at least one metadata attribute can comprise an information which part of the examination object is depicted in the medical image and/or in which orientation the part of the examination object is depicted and/or about the laterality of the part of the examination object and/or in which view the part of the examination object is imaged.

The at least one first metadata attribute can be comprised by a Digital Imaging and Communications in Medicine (DICOM) header which is associated to the medical image. With other words, the at least one first metadata attribute can be a DICOM attribute which is comprised by a DICOM header of the medical image. Alternatively, the at least one first metadata attribute can be comprised by a Neuroimaging Informatics Technology Initiative (NIfTI) header. Alternatively, the at least one first metadata attribute can be comprised by a header of the medical image, wherein the medical image can be of any other data format. The data format of the medical image can for example be Analyze or Medical Imaging Network Common Data Format (MINC).

The at least one first metadata attribute comprises an attribute tag and a provisional attribute value. The attribute tag specifies which information is comprised by the at least one first metadata attribute. For example, the attribute tag can be one out of the following: 'Body part examined', 'Anatomic Region Sequence', 'Patient Orientation', View Position', 'Image Laterality', 'Frame Laterality', 'Measurement Laterality' etc. Typically, the attribute tag cannot be changed. The provisional attribute value provides the value corresponding to the attribute tag. In particular, the provisional attribute value can be empty. The provisional attribute value can comprise a string value and/or an integer value and/or a float value and/or a free-text value. In particular, the attribute value comprises an information about the "topic" which is provided by the corresponding attribute tag.

In the following, the expression "filling in the at least one metadata attribute" means that an attribute value which is comprised by the at least one first metadata attribute is filled in. Hence, "filling in the at least one first metadata attribute" and "filling in the attribute value" are used synonymously. The provisional attribute value can be filled in manually or automatically. In particular, the provisional attribute value can be filled in manually by a medical doctor and/or a medical assistant. Alternatively or additionally, the provisional attribute value can be filled in automatically by the medical imaging system. For example, the medical imaging system can fill in the provisional attribute value based on an imaging protocol.

In the step of receiving the medical image and the at least one first metadata attribute, the medical image and the at least one first metadata attribute is received by an interface. The medical image and the at least one metadata attribute can be provided for example by a Picture Archiving and Communication System (PACS) or by a Radiology Imaging System (RIS) or by a Hospital Information System (HIS) etc.

In the step of applying the first trained function to the medical image, the first trained function is applied to the medical image, in order to determine the image-based attribute value. In particular, the attribute value corresponding to the attribute tag can be determined based on the medical image. For example, by applying the first trained function it can be determined which part of the examination object is depicted by the medical image and/or it can be determined whether for example a right or a left hand is depicted by the medical image etc.

In general, the first trained function mimics cognitive functions that humans associate with other human minds. In particular, by training based on training data the first trained function is able to adapt to new circumstances and to detect and extrapolate patterns.

In general, parameters of the first trained function can be adapted via training. In particular, supervised training, semi-supervised training, unsupervised training, reinforcement learning and/or active learning can be used. Furthermore, representation learning (an alternative term is "feature learning") can be used. In particular, the parameters of the first trained function can be adapted iteratively by several steps of training.

In particular, the first trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network, or a convolutional deep neural network. Furthermore, a neural network can be an adversarial network, a deep adversarial network and/or a generative adversarial network.

In particular, the first trained function can comprise a deep learning network (e.g. deep belief network, residual neural network, dense neural network, autoencoder, capsule network, generative adversarial network, Siamese network, convolutional neural network, image transformer network) respectively it can be based on a deep learning technique (e.g. deep reinforcement learning, landmark detection). Alternatively or additionally, the first trained function can be based on a machine learning technique (e.g. support vector machine, Bayesian model, decision tree, k-means clustering). Alternatively or additionally, the first trained function can be based on a traditional image processing technique (e.g. template matching, content based image retrieval, similarity search morphological processing).

The determined image-based attribute value can be determined based on an available ontology or a privately defined dictionary. The available ontology can for example be a standard ontology like RadLex or Systematized Nomenclature of Medicine Clinical Terms (SNOMED-CT). A privately defined dictionary can be a dictionary which comprises abbreviations and/or acronyms and/or expressions typically used by the medical doctor and/or within a hospital, where the medical image is acquired.

In the step of determining the final attribute value, the final attribute value is determined based on the provisional attribute value and the image-based attribute value. In particular the final attribute value can be determined by a comparison of the provisional attribute value and the image-based attribute value. In particular, determining the final attribute value can be performed automatically. Alternatively, determining the final attribute value can be performed manually by the medical doctor and/or the medical assistant.

In the step of providing the at least one first metadata attribute, the at least one first metadata attribute is provided by the interface. In particular, the at least one first metadata attribute is provided in association with the medical image. The at least one first metadata attribute comprises the attribute tag and the final attribute value. The at least one first metadata attribute can for example be used to query a plurality of medical images all comprising a metadata attribute comprising the same attribute value. Alternatively or additionally, the at least one first metadata attribute can be used together with the medical image for further diagnosis of the examination object. Alternatively or additionally, the at least one first metadata attribute can be used by an application which should be applied to the medical image. The application can for example be configured for image processing of the medical image. It might be necessary for applying the application to know the correct at least one first metadata attribute.

The inventors recognized that the attribute value of at least one metadata attribute associated to a medical image can be unified by applying the first trained function to the medical image. In particular, the at least one first metadata attribute can be unified based on the associated medical image. In particular unifying means in this context correcting or filling in the final attribute value of the at least one first metadata attribute value.

According to a further embodiment of the invention the method comprises a step of checking whether the provisional attribute value is empty, wherein the step of determining the final attribute value is based on the result of the check.

With other words, before determining the final attribute value based on the provisional attribute value and the image-based attribute value, it is checked whether the provisional attribute value is empty or whether it is already filled in automatically or manually. Determining the final attribute value is based on this comparison. With other words the step of determining the final attribute value is adapted to the result of the check.

If the provisional attribute value is not empty, it is necessary to decide whether the provisional attribute value or the image-based attribute value or a combination of both should be set as the final attribute value in the step of determining the final attribute value. If it is empty, the final attribute value can be set to be the image-based attribute value.

The inventors recognized that the step of determining the final attribute value can be dependent of the provisional attribute value. The inventors recognized that the final attribute value should be determined in dependence whether the provisional attribute value is empty or not.

According to a further embodiment of the invention, if the provisional attribute value is empty, the step of determining the final attribute value comprises a step of filling the final attribute value with the image-based attribute value.

With other words, if the provisional attribute value is empty, the final attribute value is chosen to be the image-based attribute value. With other words, the final attribute value can be set to be the image-based attribute value if the provisional attribute value is empty.

The inventors recognized that the final attribute value can be filled with the image-based attribute value if the provisional attribute value is empty. The inventors recognized that like this, it is possible to fill the attribute value of a metadata attribute, which is not filled in automatically or manually during the imaging process, automatically, based on the medical image. With other words, the inventors recognized that like this an autofilling based on the medical image can be performed. The inventors recognized that this helps to avoid empty attribute values. Furthermore, the inventors recognized that the effort of the medical doctor or the medical assistant and/or a potential human error can be reduced by image-based autofilling of the final attribute value.

According to a further embodiment of the invention, if the provisional attribute value is not empty, the step of determining the final attribute value comprises a step of comparing the provisional attribute value and the image-based attribute value. Therein the final attribute value is determined based on this comparison.

With other words, if the provisional attribute value is not empty, the final attribute value is determined based on a comparison of the provisional attribute value and the image-based attribute value. In particular, the comparison can be performed automatically. In particular, if the provisional attribute value and the image-based attribute value are the same, the final attribute value corresponds to the provisional attribute value and the image-based attribute value. If the provisional attribute value and the image-based attribute value are different, the final attribute value can be automatically filled by the image-based attribute value. Alternatively, the medical doctor and/or the medical assistant can be asked to check which of the attribute values should be chosen to be the final attribute value. Alternatively, the comparison can be based on a similarity-based comparison in order to determine if the provisional attribute value and the image-based attribute value are synonym to each other. If the provisional attribute value and the image-based attribute value are synonyms, the more general or the more standardized value can be set to be the final attribute value. In particular, the value corresponding to the ontology can be set to be the final attribute value.

The inventors recognized that the provisional attribute value can be automatically corrected by choosing the image-based attribute value as final attribute value. The inventors recognized that this can be confirmed by the medical doctor and/or the medical assistant. The inventors recognized that autocorrecting the at least one first metadata attribute value should be handled differently to autofilling the final attribute value of the at least one first metadata attribute. The inventors recognized that the final attribute value can depend on both the provisional attribute value and the image-based attribute value. In particular, the inventors recognized that it might be necessary to consider the provisional attribute value and the image-based attribute value, when determining the final attribute value.

According to a further embodiment of the invention the step of comparing the provisional attribute value and the image-based attribute value comprises a step of applying a second trained function to the provisional attribute value so as to determine the final attribute value.

In general, the second trained function can be designed according to the description of the first trained function. In particular, the second trained function can determine a mismatch index respectively a similarity index for comparing the provisional attribute value and the image-based attribute value. Based on this index the second trained function can be designed to determine the correct attribute value to be the final attribute value. For example, the second trained function can be designed to recognize whether the provisional attribute value and the image-based attribute value are synonym to each other. In this case, the more general respectively unified attribute value can be chosen to be the final attribute value. In particular, the correct attribute value out of the provisional attribute value and the image-based attribute value can be chosen based on the ontology or privately defined dictionary respectively individual dictionary. In case of a contradiction between the provisional attribute value and the image-based attribute value, the image-based attribute value can be preferred by the second trained function.

In an embodiment of the invention the result of the second trained function can be confirmed or rejected by the medical doctor and/or the medical assistant and/or the technologist.

The inventors recognized that the comparison of the provisional attribute value and the image-base attribute value can be performed by applying the second trained function. They recognized that the second trained can be trained to determine a similarity measure respectively index in order to identify synonyms. The inventors recognized that like this the most general respectively unified attribute value can be determined to be the final attribute value based on the provisional attribute value and the image-based attribute value. The inventors recognized that an incorrect provisional attribute value can be corrected by filling the final attribute value with the image-based attribute value in the case of a contradiction between the provisional attribute value and the image-based attribute value. The inventors recognized that filling in the final attribute value can be controlled by the medical doctor and/or the medical assistant.

According to a further embodiment of the invention the first trained function comprises the second trained function.

With other words, the first trained function is designed to perform both steps of determining the image-based attribute value and of determining the final attribute value. In this case the first trained function can be applied to the medical image and the provisional attribute value. The final attribute value is the output of the first trained function in this embodiment.

In particular, the first trained function can consider the provisional attribute value when determining the image-based attribute value in this case. The image-based attribute value which is determined by considering the provisional attribute value can be set to be the final attribute value.

Alternatively, the first trained function can determine the image-based attribute value independently of the provisional attribute value. In this case, the first trained function can determine the final attribute value in an independent step by comparing the provisional attribute value and the image-based attribute value. This step can be performed as described above for the second trained function.

In other words, the first trained function can depend on whether the provisional attribute value is empty or not.

The inventors recognized that the whole procedure for determining the final attribute value for the case that the provisional attribute value is not empty can be performed by one, the first trained function. In particular, this first trained function can be trained in one step.

According to a further embodiment of the invention the method comprises a step of selecting the first trained function from a plurality of first trained functions based on the result of the check and/or the attribute tag.

In the step of selecting the first trained function the first trained function which should be applied to the medical image is selected based on the result of the step of checking whether the provisional attribute value is empty and/or based on the attribute tag. The plurality of first trained functions can be received in a step of receiving the plurality of first trained functions.

Each first trained function of the plurality of first trained functions can be related to a specific attribute tag. With other words a first trained function of the plurality of first trained function can be trained to determine the image-based attribute value in a specific context. The attribute tag defines the context of the image-based attribute value which should be determined by applying the first trained function. For example, a first trained function can be designed to determine the image-based attribute value related to the attribute tag, which specifies the imaged part of the examination object. Another trained function can be designed to determine the laterality of the examination object. Hence, this trained function can be suitable for determining the image-based attribute value related to the attribute tag which specifies the laterality. Thus, the first trained function which is suited for determining the image-based attribute value for the at least one first metadata attribute can be selected based on the corresponding attribute tag.

Alternatively or additionally, the first trained functions can differ concerning their applicability for comparing the provisional attribute value and the image-based attribute value in the case that the provisional attribute value is not empty. With other words, the applicability of a first trained function of the plurality of first trained functions can depend in the fact whether the provisional attribute tag is empty or not. Hence, it depends on the result of the check. With other words, at least one first trained function of the plurality of first trained function can be suited to perform the step of determining the image-based attribute value and of determining the final attribute value as it is described above for the case that the provisional attribute value is not empty. The output of this first trained function is the final attribute value. Alternatively or additionally, at least one other first trained function is only suited for determining the image-based attribute value. In this case the output of the first trained function is the image-based attribute value. This first trained function can in particular be applied if the provisional attribute value is empty. Then the step of determining the final attribute value can be performed independently of the trained function. In particular, this first trained function can also be applied if the provisional attribute value is not empty, for the case that the final attribute value is determined in a step of comparing the provisional attribute value and the image-based attribute value independently of the first trained function as described above.

With other words, some of the trained functions of the plurality of trained functions might be suited to provide the image-based attribute value. This image-based attribute value can then be determined to be the final attribute value if the provisional attribute value is empty. Alternatively, the image-based attribute value can be used for the step of comparing the provisional attribute value and the image-based attribute value. The other trained functions of the plurality of trained functions can comprise the second trained function. Hence, these trained functions are suitable if the final attribute value should be determined directly by applying the first trained function and if the provisional attribute value is not empty.

The inventors recognized that there can be a plurality of specific trained functions wherein each can be suited for a specific case concerning the attribute tag and the provisional attribute value. The inventors recognized that the first trained function is one of the plurality of first trained functions. The inventors recognized that the first trained function is the trained function of the plurality of first trained functions which fulfills the requirements concerning its suitability with respect to the attribute tag and/or the result of the check.

According to a further embodiment of the invention a plurality of metadata attributes is associated to the medical image. Therein each metadata attribute of the plurality of metadata attributes comprises an attribute tag and an attribute value. Therein the first metadata attribute is one metadata attribute of the plurality of metadata attributes. Therein, the method further comprises the step of determining the at least one first metadata attribute out of the plurality of metadata attributes based on an application configured to process the medical image and/or on the attribute tags.

In particular, the plurality of metadata attributes describes respectively specifies the medical image. With other words a metadata attribute can describe a property of the medical image. Alternatively or additionally, a metadata attribute can describe a property the acquisition process of the medical image. In particular, each metadata attribute can describe another property of the medical image. In particular, each metadata attribute of the plurality of metadata attributes can be designed like the at least one first metadata attribute. Wherein each metadata attribute relates to another context concerning the medical image.

In the step of receiving the at least one first metadata attributes all metadata attributes of the plurality of metadata attributes can be received. The at least one first metadata attribute can be determined out of the plurality of metadata attributes in the step of determining the at least one first metadata attribute.

The at least one metadata attribute can in particular be determined based on an application configured to process the medical image. In particular, the application can be configured to perform some image processing based on the medical image. The application can for example be configured to determine a diagnosis based on the medical image. The application can need the at least one first metadata attribute as input value. For this purpose, it is necessary that the at least one first metadata attribute is correct and complete. Furthermore, it is necessary that the at least one metadata attribute is unified. Hence, it is known in advance, that when applying the application to the medical image, it is necessary, that the at least one first metadata attribute comprising a specific attribute tag is correctly filled. The application can pre-define the at least one first metadata attribute which it needs as input value, by the corresponding attribute tag. Hence, the at least one first metadata attribute can be determined based on the corresponding attribute tag. With other words, the at least one first metadata attribute can be chosen respectively selected out of the plurality of metadata attributes based on the attribute tag provided respectively pre-defined by the application.

Alternatively or additionally, the at least one first metadata attribute can be determined based on the attribute tags. In particular, the at least one first metadata attribute has to be determined based on the medical image. With other words, the final attribute value of the at least one first metadata attribute has to be suited to be determined based on the associated medical image. There might be some metadata attributes within the plurality of metadata attributes which are not suited to be determined based on the medical image like for example the date the medical image was taken. Hence, the at least one first metadata attribute is one of the plurality of metadata attributes, that can be determined based on the medical image.

The inventors recognized that a plurality of metadata attributes can be associated to the medical image. They recognized that not all metadata attributes of this plurality of metadata attributes are suited to be filled in based on the medical image. They recognized that the attribute tags can be used to identify those metadata attributes whose final attribute values are suited to be determined based on the associated medical image. They furthermore recognized that it might be sufficient to determine the final attribute value of just some of the metadata attributes based on the further processing of the medical image. Therein the further processing can be performed by the application.

According to a further embodiment of the invention a plurality of metadata attributes is associated to the medical image. Therein the at least one first metadata attribute is one metadata attribute of the plurality of metadata attributes. Therein the method comprises the step of receiving at least one second metadata attribute of the plurality of metadata attributes, wherein the at least one second metadata attribute is related to the at least one first metadata attribute. Therein the first trained function is also applied to the at least one second metadata attribute in the step of applying the first trained function.

The plurality of metadata attributes can be designed as above described. Each of the metadata attributes of the plurality of metadata attributes comprises an attribute tag and an attribute value. The at least one first metadata attribute and the at least one second metadata attribute are each one of the plurality of metadata attributes.

In the step of receiving the at least one second metadata attribute the at least one second metadata attribute is deceived by the interface. The at least one second metadata attribute can be determined and provided by the claimed method in advance. The at least one second metadata attribute is related to the at least one first metadata attribute. In particular, the at least one second and the at least one first metadata attribute are in the same field respectively context. In particular, the at least one second metadata attribute relates to a more generalized embodiment of the embodiment described by the at least one first metadata attribute. For example, the at least one second metadata attribute comprises the attribute tag 'body part'. Then the corresponding attribute value can be 'thorax'. The at least first metadata attribute in this context can comprise the attribute tag 'organ'. Then the corresponding final attribute value can be 'heart'. Hence, the at least one second metadata attribute can be used as pre-knowledge for determining the final attribute value. In this example, the first trained function can use the knowledge that the searched organ has to be in the thorax for determining the image-based attribute value. In this case, it is known in advance that the attribute value of the at least one first metadata attribute cannot be 'brain' if the attribute value of the at least one second metadata attribute is 'thorax'. Hence, the first trained function is applied to the medical image and the at least one second metadata attribute.

In another example, the at least one second metadata attribute can comprise 'organ' as attribute tag and 'heart' as attribute value. Then the first trained function can recognize that the image-based attribute value of the at least one first metadata attribute comprising the attribute tag 'laterality' should be empty, as the heart shows no laterality.

The inventors recognized that the knowledge of at least one second metadata attribute which is in the same field as the at least one first metadata attribute can be used as pre-knowledge for determining the final attribute value. In particular, the at least one second metadata attribute value can be used as input for the first trained function. Furthermore, they recognized that the at least one second metadata attribute can be used to determine whether it makes sense to determine the image-based attribute value of the at least one first metadata attribute.

According to an optional embodiment of the invention, the step of selecting the first trained function from a plurality of first trained functions is based on the at least one second attribute.

In particular, according to the example above, a first trained function can be selected which is suited to identify the imaged organ within a thorax in the medical image. With other words, the at least one second metadata attribute can provide an information about the field respectively the context in which the first trained function should be able to fill in the at least one first metadata attribute. In the example above, the at least one second metadata attribute defines the body region for which the first trained function should be specialized in order to determine the imaged organ for determining the image-based attribute value. With other words, the at least one second metadata attribute can be used as information about the field respectively the context, the first trained function should be specialized in for determining the image-based attribute value of the at least one first metadata attribute.

The inventors recognized that the at least one second metadata attribute can be suited for selecting the correct first trained function. With other words, the inventors recognized that the at least one second metadata attribute can define the context respectively the field the at least one first metadata attribute is in. The first trained function should be suited to determine the image-based attribute value with regard to the respective context respectively field.

According to a further embodiment of the invention the provisional attribute value comprises a free-text attribute value. Therein the method comprises a step of standardizing the free-text attribute value by applying a third trained function to the at least one first metadata attribute, wherein the free-text attribute value is replaced by the standardized attribute value in the provisional attribute value of the at least one first metadata attribute.

The free-text attribute value can comprise a string value. The free-text attribute value can be provided manually by the medical doctor and/or the medical assistant. The free-text attribute value can comprise at least one not standardized expression and/or at least one abbreviation and/or at least one acronym.

In general, the third trained function can be designed according to the description of the first trained function. The third trained function can be designed to perform a clinical word sense disambiguation. The third trained function can in particular be designed to replace an attribute value comprising e.g. an acronym and/or an abbreviation by a more standardized attribute value without manipulating the meaning of the attribute value. The third trained function can be based on a natural language processing technique like word embedding, word-level convolutional neural network, bi-direction long short-term memory network, recurrent neural network, dictionary learning and/or an image transformer network. Alternatively or additionally, the third trained function can be based on a machine learning technique like support vector machine, Bayesian model, decision tree and/or k-means clustering. Alternatively or additionally, the third trained function can be based on any other traditional text analyses or comparison technique like an edit-based similarity metric like Levenshtein distance and/or a token-based similarity metric and/or a sequence-based similarity matric and/or a phonetic approach.

The standardized attribute value can be based on a standard ontology like RadLex and/or SNOMED-CT. Alternatively or additionally the standardized attribute value can be determined based on a privately defined dictionary respectively lexicon. The privately defined dictionary can be specific for the medical doctor or for a clinic respectively hospital. The privately defined dictionary can comprise individual abbreviations and/or expressions of the medical doctor and their general respectively standardized pendant. An example for a free-text attribute value can be 'Thx p.a. LR ER'. The corresponding standardized attribute value can be 'Thorax Posterior Anterior Left Right Emergency Room'. Another example for a free-text attribute value can be 'Chest AP Port'. The corresponding standardized attribute value can be 'Chest anterior posterior portable'.

The provisional attribute value comprising the standardized attribute value can be used for determining the final attribute value as described above. In particular, the at least one second metadata attribute can be determined by standardizing an attribute value of the at least one second metadata attribute as described above. In particular, standardizing the attribute value of the at least one second metadata attribute can be performed in advance, before determining the image-based attribute value of the at least one first metadata attribute.

The inventors recognized that before correcting the provisional attribute value by determining an image-based attribute value and by comparing the image-based attribute value, it might be helpful to first standardize the provisional attribute value. Like this, comparing the attribute values is easier. Furthermore, even if the provisional attribute value is set to be the final attribute value, for further processing the medical image based on the corresponding at least one first metadata attribute, it might be helpful if the final attribute value is standardized. Like this, the final attribute value can be used as input for an application as described above and/or for querying based on the final attribute value.

According to a further embodiment of the invention the method further comprises a step of categorizing the standardized attribute value by applying a fourth trained function to the at least one metadata attribute. Therein the standardized attribute value is replaced by the categorized standardized attribute value in the provisional attribute value of the at least one first metadata attribute.

In general, the fourth trained function can be designed as described according to the first trained function. The fourth trained function can be designed to classify the unstructured text comprised by the standardized attribute value into pre-defined categories like anatomical entity, clinical finding, imaging modality, imaging observation, procedure and/or non-anatomical entities etc. In particular, the single words comprised by the standardized attribute value can be categorized by applying the fourth trained function to the standardized attribute value. In particular, each word or each expression comprised by the standardized attribute value can be assigned to a category.

The fourth trained function can be based on clinical named entity recognition. The fourth trained function can be based on a linguistic grammar technique using a natural language processing technique like word embedding, word-level convolutional neural network, bi-direction long short-term memory network, recurrent neural network and or dictionary learning. Alternatively or additionally, the fourth trained function can be based on a machine learning technique like support vector machine, Bayesian model, decision tree and/or k-means clustering. Alternatively or additionally, the fourth trained function can be based on any other traditional text analyses or comparison technique like an edit-based similarity metric like Levenshtein distance and/or a token-based similarity metric and/or a sequence-based similarity matric and/or a phonetic approach.

In the above described example, the expressions of the standardized attribute value 'Thorax Posterior Anterior Left Right Emergency Room' can be categorized as following: [Thorax]→'Anatomy', [Posterior Anterior]→'View Position', [Left Right]→'Patient Orientation', [Emergency Room]→'Location'. The standardized attribute value 'Chest Anterior Posterior Portable' of the other example from above can be categorized as following: [Chest]→'Anatomy', [Anterior Posterior]→'View Position', [Portable]→'Modality'.

The provisional attribute value comprising the categorized standardized attribute value can be used for determining the final attribute value as described above. In particular, the at least one second metadata attribute can be determined by categorizing and/or standardizing an attribute value of the at least one second metadata attribute as described above. In particular, categorizing and/or standardizing the attribute value of the at least one second metadata attribute can be performed in advance, before determining the image-based attribute value of the at least one first metadata attribute.

The inventors recognized that for further processing the medical image and/or the at least one first metadata attribute, it might be helpful if the expressions of the standardized attribute values are categorized. In particular, this can help searching respectively querying a plurality of medical images with associated metadata attributes. Furthermore, the categorized standardized attribute value can be used to fill in the attribute values of other metadata attributes associated with the medical image according to the category. With other words, the attribute value of a metadata attribute whose attribute tag is related to a category can be filled in by the standardized expression which is related to the category within the standardized attribute value.

According to a further embodiment of the invention the method comprises a step of performing a semantic matching of the categorized standardized attribute value with higher-level terms by applying a fifth trained function to the at least one metadata attribute. Therein the categorized standardized attribute value is replaced by the matched categorized standardized attribute value in the provisional attribute value of the at least one first metadata attribute.

In an alternative embodiment a matched standardized attribute value is determined by applying the fifth trained function to the at least one first metadata attribute, wherein the corresponding provisional attribute value comprises the standardized attribute value. Therein the standardized attribute value is replaced by the matched standardized attribute value in the provisional attribute value of the at least one first metadata attribute.

The fifth trained function is based on semantic matching. In particular the fifth trained function is designed to map semantically similar terms to a standardized text e.g. based on a standard ontology like RadLex and/or SNOMED-CT and/or based on a privately defined dictionary. In general, the fifth trained function can be designed according to the description of the first trained function above. The fifth trained function can be based on a natural language processing technique like word embedding, word-level convolutional neural network, bi-direction long short-term memory network, recurrent neural network and or dictionary learning. Alternatively or additionally, the fifth trained function can be based on a machine learning technique like support vector machine, Bayesian model, decision tree and/or k-means clustering. Alternatively or additionally, the fifth trained function can be based on any other traditional text analyses or comparison technique like an edit-based similarity metric like Levenshtein distance and/or a token-based similarity metric and/or a sequence-based similarity matric and/or a phonetic approach.

The higher-level terms describe the expressions comprised by the categorized standardized attribute value respectively the standardized attribute value in a more general respectively unified way. In the example above the categorized standardized attribute value is 'Thorax Posterior Anterior Left Right Emergency Room'. The categories have been omitted to enhance the clarity. The matched categorized standardized attribute value is 'Chest Posterior Anterior Left Right Emergency Room'. Hence, the expression 'Thorax' is replaced by the more general higher-level term 'Chest'. In the other example the categorized standardized attribute value is 'Chest Anterior Posterior Portable'. Again, the categories are omitted due to clarity. The matched categorized standardized attribute value is 'Chest Anterior Posterior Portable X-Ray'. Hence, the expression 'Portable' is replaced by the higher-level term 'Portable X-Ray' as it is defined in an ontology.

The provisional attribute value comprising the matched categorized standardized attribute respectively the matched standardized attribute value can be used for determining the final attribute value as described above. In particular, the at least one second metadata attribute can be determined by matching and/or categorizing and/or standardizing an attribute value of the at least one second metadata attribute as described above. In particular, matching and/or categorizing and/or standardizing the attribute value of the at least one second metadata attribute can be performed in advance, before determining the image-based attribute value of the at least one first metadata attribute.

The inventors recognized that searching respectively querying in a plurality of medical images associated to metadata attributes comprising a matched categorized standardized attribute value or a matched standardized attribute value is more convenient as the single expressions of the attribute values are all comparable.

The steps of standardizing the free-text attribute value, of categorizing the standardized attribute value and of performing a semantic matching of the categorized standardized attribute value can be applied for metadata attributes which are not associated to a medical image like Health Level 7 (HL7) messages or Fast Healthcare Interoperability Resources (FHIR). In this case, the steps which are based on an analysis of the medical image can be omitted in order to determine the final attribute value. In particular, in this case, the standardized attribute value or the categorized standardized attribute value or the matched categorized standardized attribute value can be set to be the final attribute value.

In a second embodiment the invention relates to a unifying system for providing at least one first metadata attribute associated with a medical image. The unifying system comprises an interface and a computation unit. Therein the interface is configured for receiving the medical image and the at least one first metadata attribute. Therein the at least one first metadata attribute comprises an attribute tag and a provisional attribute value. Therein the computation unit is configured for applying a first trained function to the medical image so as to determine an image-based attribute value. Therein the computation unit is configured for determining a final attribute value based on the provisional attribute value and the image-based attribute value. Therein the interface is configured for providing the at least one metadata attribute. Therein the at least one metadata attribute comprises the attribute tag and the final attribute vale.

In particular, the unifying system can be configured to execute the previously described method for providing at least one first metadata attribute associated with a medical image. The unifying system is configured to execute this method and its embodiments by the interface and the computation unit being configured to execute the corresponding method steps. In particular, the interface can comprise one or more sub-interfaces. In particular, the computation unit can comprise one or more computation sub-units.

In a third embodiment the invention relates to a computer program product with a computer program and a computer-readable medium. A mainly software-based implementation has the advantage that even previously used unifying systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a further embodiment the invention relates to a computer program product comprising program elements directly loadable into a memory unit of a first providing system, which induces the unifying system to execute the method according to the claimed method and its embodiments when the program elements are executed by the unifying system.

In a fourth embodiment the invention relates to a computer-readable storage medium comprising program elements which are readable and executable by a unifying system, to execute the claimed method and its embodiments, when the program elements are executed by the unifying system.

In a further optional embodiment the invention relates to a computer-implemented method for providing a first trained function. The method comprises receiving input training data, wherein the input training data comprises a medical training-image and at least one first metadata training-attribute associated with the medical training-image. The method comprises receiving output training data, wherein the output training data comprises a final training-attribute value. Therein the output training data is related to the input training data. The method comprises training a first function based on the input training data and the output training data. The method comprises providing the first trained function.

The output training data can be determined based on the input training data by manual annotation. With other words, the final training-attribute value of the at least one first training-attribute can be determined by a medical doctor and/or a medical assistant.

FIG. 1 displays a schematic flow chart of a first embodiment of the method for providing at least one first metadata attribute associated with a medical image.

The medical image is acquired with a medical imaging system. The medical imaging system can be for example one out of the following: X-ray system, a Computed-Tomography (CT) system, a Magnetic-Resonance-Imaging (MRI) system, an angiography system, a C-arm system, an ultrasonic system, a Positron-Emission-Tomography (PET) system, a Single-Photon-Emission-Computed-Tomography (SPECT) system. The medical image comprises a pixelmatrix or a voxelmatrix. Therein the pixelmatrix respectively the voxelmatrix comprises a plurality of pixels or voxels. Hence, the medical image is a two-dimensional or a three-dimensional medical image. Alternatively, the medical image can be a four-dimensional medical image. Therein the four-dimensional medical image can in particular comprise a time-series of three-dimensional medical images.

The medical image depicts an examination object. The examination object is a patient. Alternatively, the examination object can be an animal or an object. The medical image can depict a part of the examination object. For example, the medical image can depict an organ or an extremity of the patient. With other words the medical image can depict a part respectively a body part of the examination object.

The medical image is associated with at least one first metadata attribute. In this embodiment, the at least one first metadata attribute is a DICOM attribute. The DICOM attribute is comprised by a DICOM header of the medical image. Alternatively, the at least one first metadata attribute can be a NIfTI attribute which is comprised by a NIfTI header. The at least one first metadata attribute characterizes the medical image. In particular, the at least one first metadata attribute describes which medical imaging system is used for acquiring the medical image, which parameters are used for acquiring the medical image, who or what is imaged, what exactly is the examination object depicted in the medical image, how is the examination object imaged etc. The at least one first metadata attribute comprises an attribute tag and an attribute value. The attribute tag defines the context respectively the field of the at least one metadata attribute. With other words the attribute tag defines what the at least one first metadata attribute refers to. For example, the attribute tag can be 'Body part examined', 'Anatomic Region Sequence', 'Patient Orientation', View Position', 'Image Laterality', 'Frame Laterality', 'Measurement Laterality' etc. The attribute value can provide the specific value concerning the attribute tag and the medical image. For example, the attribute tag can be 'Body part examined'. Then the corresponding attribute value can be 'Thorax' if the associated medical image comprises an image of a thorax. The at least one first metadata attribute can be for example used to query a database for all medical images which are associated to a metadata attribute comprising the attribute tag 'Body part examined' and the attribute value 'Thorax'. Then these medical images can be compared or further processed. Alternatively or additionally, the at least one first metadata attribute can be used as input value by an application which is applied to the medical data. For example, the application can be configured to provide a diagnosis based on the medical image. In this context, the at least one first metadata attribute can provide an information which body part is shown on the medical image. This information can be used by the application for determining the diagnosis.

In a step of receiving REC-1 the medical image and the at least one first metadata attribute, the medical image and the at least one first metadata attribute is received by an interface SYS.IF.

The at least one first metadata attribute comprises an attribute tag and a provisional attribute value. The provisional attribute value of the at least one first metadata attribute can be filled automatically during the imaging process or manually by a medical doctor and/or a medical assistant. Alternatively, the provisional attribute value can be empty.

In a step of applying APP-1 a first trained function to the medical image, the first trained function is applied to the medical image in order to determine an image-based attribute value. The image-based attribute value is related to the attribute tag. The image-based attribute value is, therefore, determined based on the medical image. For example, the imaged body part can be determined by applying the first trained function to the medical image if the attribute tag of the at least one first metadata attribute is 'Body part examined'. The result of the first trained function is the image-based attribute value.

The first trained function can determine the image-based attribute value based on an ontology or a privately defined dictionary. The ontology can for example comprise RadLex and/or SNOMED-CT. The privately defined dictionary can be defined by a medical doctor and/or a medical assistant and/or for a clinical staff. The privately defined dictionary can comprise terms and expressions typically used by the medical doctor and/or the medical assistant and/or the medical staff.

In a step of determining DET-1 a final attribute value, the final attribute value is determined based on the provisional attribute value and the image-based attribute value. In particular, the final attribute value can be determined to be the image-based attribute value. With other words, the final attribute value can be set to be the image-based attribute value. Alternatively, the final attribute value can be determined based on a comparison of the provisional attribute value and the image-based attribute value. With other words the final attribute value can consider both, the provisional attribute value and the image-based attribute value.

In a step of providing PROV the at least one first metadata attribute, the at least one first metadata attribute comprising the attribute tag and the final attribute value is provided via the interface SYS.IF. In particular, the at least one first metadata attribute is provided in association with the medical image. The at least one first metadata attribute can be used by the application for further processing of the medical image. Alternatively or additionally, the at least one first metadata attribute can be used to compare or query a plurality of medical images within a database, wherein the medical image is one of the plurality of medical images.

FIG. 2 displays a schematic flow chart of a second embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1.

The embodiment of the method comprises a step of checking CHECK whether the provisional attribute value is empty.

As described above, the provisional attribute value can be filled in automatically or manually during the imaging process. In this case, it should be checked whether the provisional attribute value is correct and if it fits to the medical image. This can be done by comparing the provisional attribute value to the image-based attribute value. Hence, in this case the final attribute value can depend on the provisional attribute value and the image-based attribute value. The final attribute value should comprise the correct attribute value.

Alternatively, the provisional attribute can be empty. In this case, it is not necessary to compare the image-based attribute value and the provisional attribute value. Hence, the final attribute value should comprise at least the image-based attribute value.

Hence, the step of determining DET-1 of the final attribute value depends on the result of the step of checking CHECK whether the provisional attribute value is empty.

FIG. 3 displays a schematic flow chart of a third embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2.

In this embodiment, the step of determining DET-1 the final attribute value comprises a step of filling FILL the final attribute value with the image-based attribute value. The step of filling FILL the final attribute value with the image-based attribute value is applied in dependence of the result of the step of checking CHECK whether the provisional attribute value is empty. If this check is positive, the final attribute value filled with the image-based attribute value. With other word, if the provisional attribute value is empty, the final attribute value is set to be the image-based attribute value.

Figure 4:
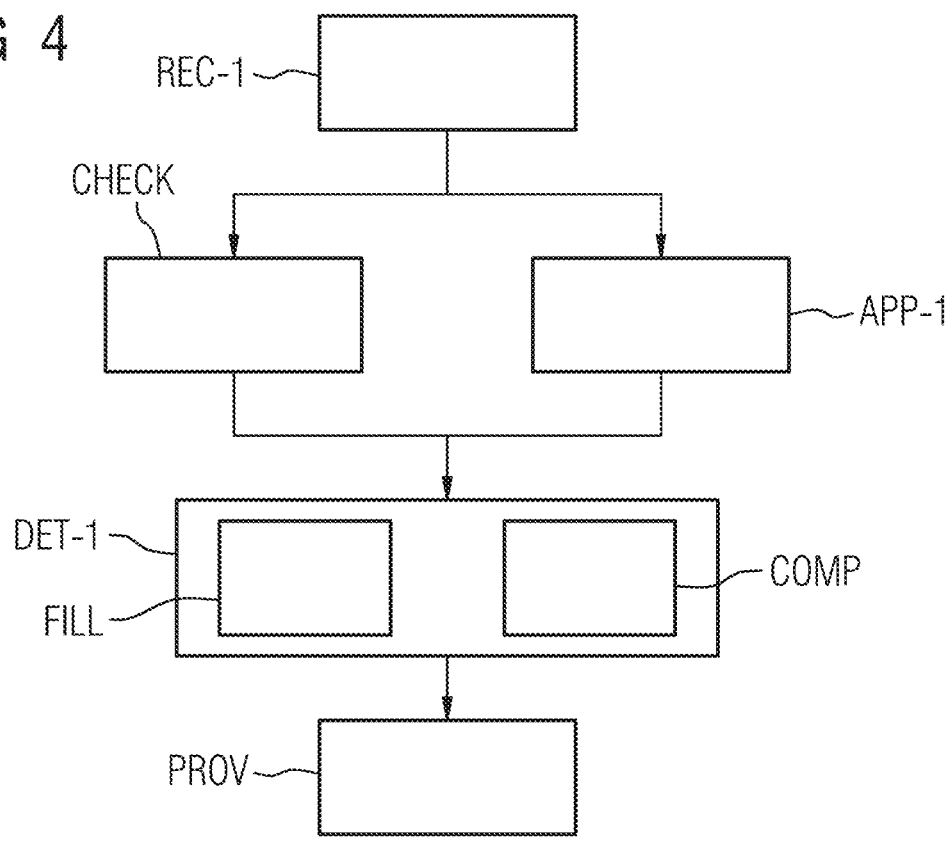

FIG. 4 displays a schematic flow chart of a fourth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3.

In this embodiment step of determining DET-1 the final attribute value comprises a step of comparing COMP the provisional attribute value and the image-based attribute value. The step of comparing COMP the provisional attribute value and the image-based attribute value is performed in dependence of the result of the step of checking CHECK whether the provisional attribute value is empty. The step of comparing COMP the provisional attribute value and the image-based attribute value is performed if the provisional attribute value is not empty. Hence, the final attribute value is determined based on both the provisional attribute value and the image-based attribute value. In particular, the final attribute value is determined based on the comparison of the provisional attribute value and the image-based attribute value. The comparison can comprise a similarity-based comparison. Based on that comparison, it can be determined if the provisional attribute value and the image-based attribute value are synonyms. If both attribute values are synonyms, the final attribute value can be filled by the more general, more standardized, more unified attribute value. This can for example be based on a standard ontology like RadLex or SNOMED-CT. If the attribute values are no synonyms, a medical doctor and/or a medical assistant can be asked to choose the correct attribute value as final attribute value. Alternatively, the image-based attribute value can in any case assumed to be the correct one. In this case, the image-based attribute value can be set to be the final attribute value.

Figure 5:
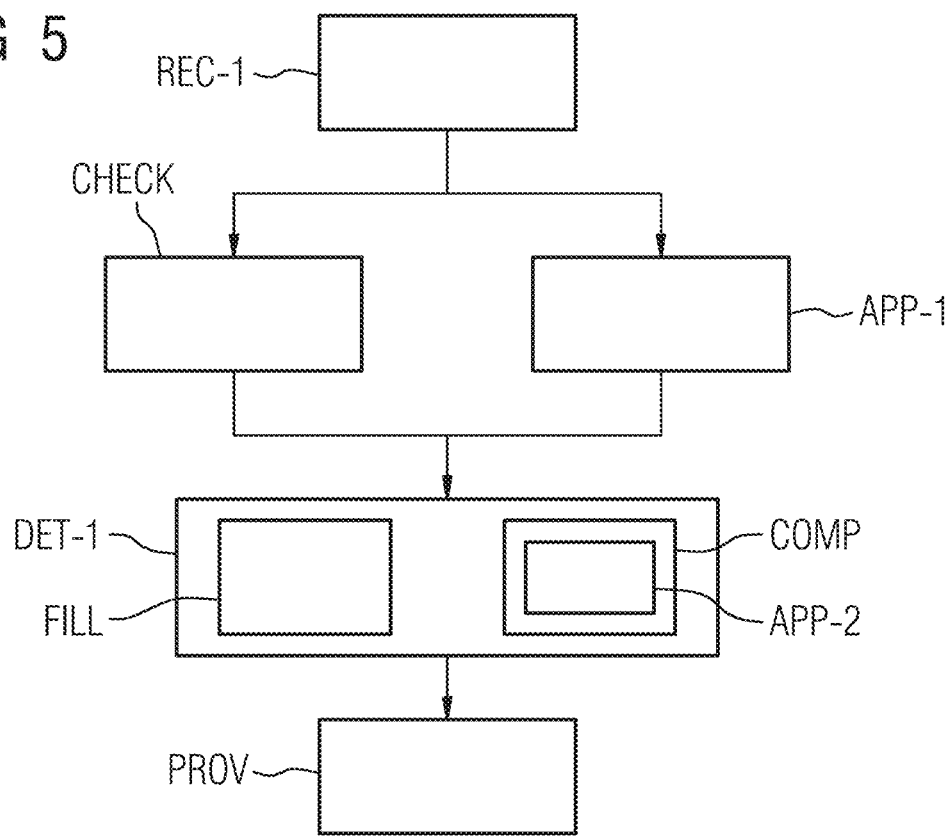

FIG. 5 displays a schematic flow chart of a fifth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4.

In this embodiment, the step of comparing COMP the provisional attribute value and the image-based attribute value comprises a step of applying APP-2 a second trained function to the provisional attribute value and the image-based attribute value in order to determine the final attribute value. With other words, the step of comparing COMP the provisional attribute value and the image-based attribute value is performed by applying the second trained function to the provisional attribute value and the image-based attribute value. In particular, the provisional attribute value and the image-based attribute value are the input data of the second trained function. In particular, the output of the second trained function is the final attribute value. The second trained function can be trained to determine the proper attribute value to be the final attribute value. The proper attribute value can be found based on the medical image. With other words, the second trained function can check whether the provisional attribute value and/or the image-based attribute value make sense with respect to the medical image. In particular, the second trained function can be trained to determine the more general respectively standardized attribute value to be the final attribute value. Alternatively or additionally, the second trained function can be trained to determine a final attribute value considering both, the provisional attribute value and the image-based attribute value. In this case, the final attribute value can be a meaningful combination of the provisional attribute value and the image-based attribute value.

In an embodiment of the invention, the first trained function can comprise the second trained function. In this case, determining the final attribute value can be performed by one trained function based on the medical image and the provisional attribute value. In particular, the first trained function comprising the second trained function can be applied to the medical image and the provisional attribute value. The output of the first trained function comprising the second trained function is the final attribute value. In this case, the first trained function comprising the second trained function can be trained in one step. If the second trained function is separate of the first trained function, each trained function has to be trained separately. In the embodiment of the first trained function comprising the second trained function, the image-based attribute value can be determined considering the provisional attribute value. In this case the step of comparing COMP the provisional attribute value and the image-based attribute value can be omitted as the image-based attribute value already considers the provisional attribute value and, hence, the image-based attribute value can assumed to be the final attribute value.

Figure 6:
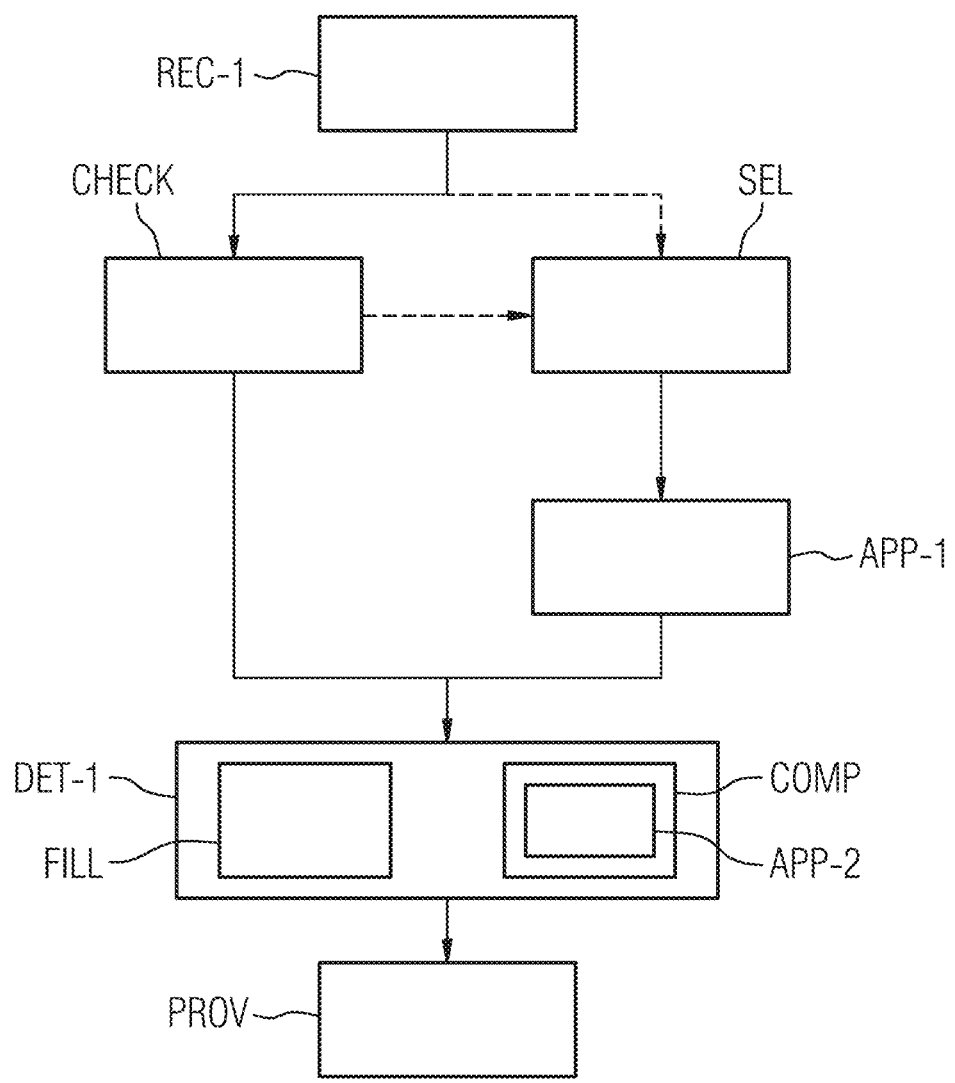

FIG. 6 displays a schematic flow chart of a sixth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5.

In this embodiment, the method comprises the step of selecting SEL the first trained function from a plurality of first trained functions based on the result of the check and/or the attribute tag. The optional dependency of the step of selecting SEL of the result of the step of checking CHECK is depicted by the dashed arrow. Accordingly, the optional dependency of the step of selecting SEL of the attribute tag is depicted by the dashed arrow between the step of receiving REC-1 the medical image and the at least one first metadata attribute and the and the step of selecting SEL.

The step of selecting SEL the first trained function can, in particular, comprise a step of receiving the plurality of first trained functions. In particular, each first trained function of the plurality of first trained functions can be designed for a specific use case. For example, a first trained function can be designed to determine a depicted body part within a thorax of the examination object. Another first trained function can be designed to determine the laterality of the examination object, and so on. The use case in question is defined by the attribute tag. For example, the attribute tag can be 'Body part examined'. In this case, a first trained function is selected which is designed respectively suited for determining an imaged body part within the medical image.

Alternatively or additionally, at least one first trained function of the plurality of first trained functions can comprise the second trained function. Hence, this first trained function is suited to be applied to the medical image and the provisional attribute if the provisional attribute is not empty. It might not be suited if the provisional attribute is empty. For this case, another first trained function of the plurality of first trained functions can be suited to be applied to the medical image. Hence, it can depend on whether the provisional attribute value is empty which first trained function of the plurality of trained functions is suited to determine the image-based attribute value respectively the final attribute value. With other words, the right first trained function in dependence of the use case can be selected based on the result of the step of checking CHECK whether the provisional attribute value is empty.

Hence, the first trained function to be used can be selected based on the use case which is defined by the attribute tag and/or based on the information if the provisional attribute value is empty or not.

Figure 7:
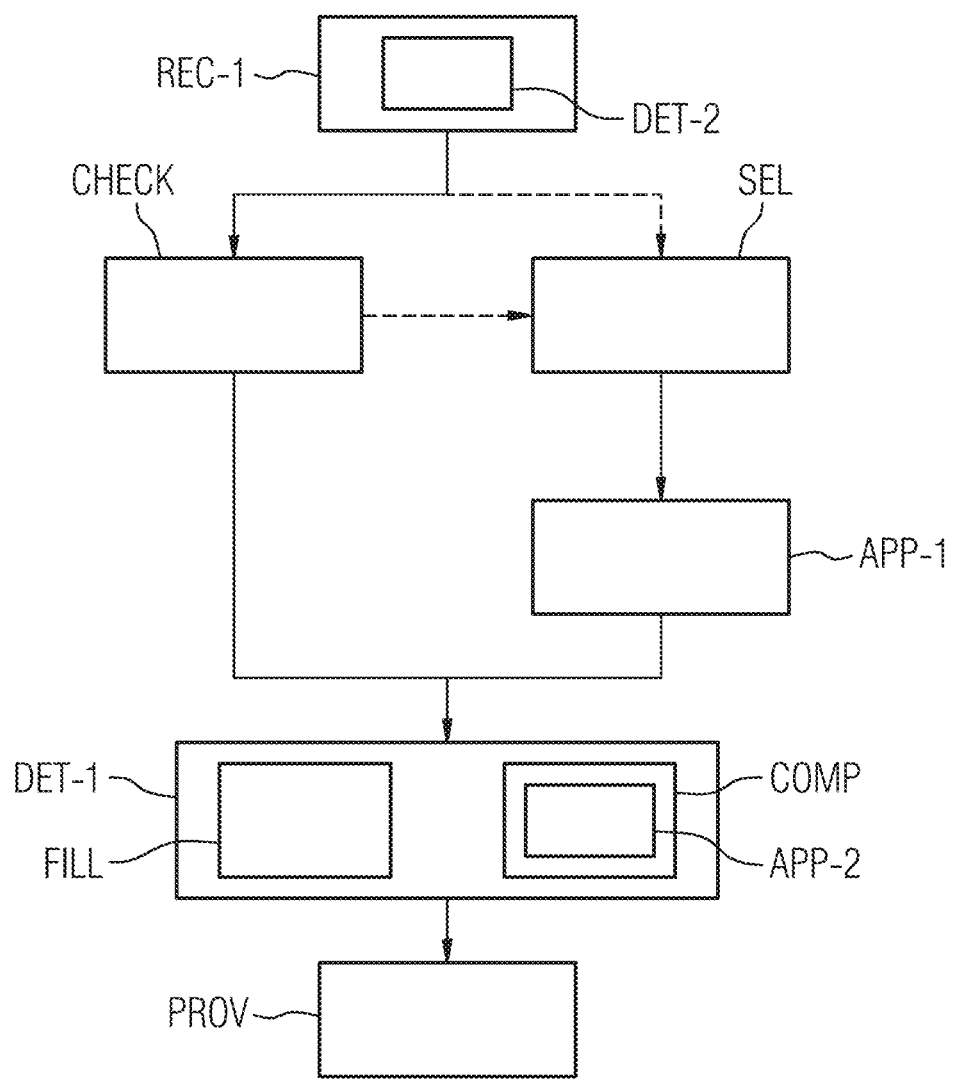

FIG. 7 displays a schematic flow chart of a seventh embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5. The step of selecting SEL the first trained function can be performed according to FIG. 6.

In this embodiment, the step of receiving REC-1 the medical image and the at least one first metadata attribute comprises a step of determining DET-2 the at least one first metadata attribute out of a plurality of metadata attributes based on an application configured to process the medical image and/or on the attribute tags.

The plurality of metadata attributes is associated to the medical image. Each metadata attribute comprises an attribute tag and an attribute value. Therein the attribute tag describes a property of the medical image the corresponding metadata attribute refers to and the corresponding attribute value provides a value according to this property. Alternatively, the attribute value can be empty. The at least one first metadata attribute is one of the plurality of metadata attributes. The plurality of metadata attributes can be received in a separate step.

In the step of determining DET-2 the at least one first metadata attribute, the at least one first metadata attribute is determined out of the plurality of metadata attributes. In particular, the at least one first metadata attribute can be a metadata attribute that is needed for further processing the associated medical image. For example, the further processing can be performed by an application. The application can be configured to process the medical image. For example, the application can be configured to make some diagnosis and/or some predictions respectively prognosis based on the medical image. The application can be configured such that it needs the at least one first metadata attribute as input data respectively as input value. For example, the application for providing some diagnosis based on the medical image needs an information about the laterality as input data. Thus, the application can for example differ between a broken bone in the right or in the left hand. This information can be provided by the metadata attribute comprising the attribute tag 'Laterality' and the corresponding attribute value. Hence, it is essential that the corresponding attribute value is correct and that it is not empty when applying the described application. Hence, the respective metadata attribute can be determined to be the at least one first metadata attribute. Hence, the at least one first metadata attribute can be a metadata attribute which is pre-defined by an application that should be applied afterwards to the medical image and that needs the at least one first metadata attribute as input data.

Alternatively or additionally, the attribute tags of the plurality of metadata attributes can be considered when determining DET-2 the at least one first metadata attribute. In particular, not all metadata attributes might be suitable for being filled and/or corrected by the method described above. For example, an information about the date of acquiring the medical image can be comprised by a metadata attribute of the plurality of metadata attributes. With other words, the corresponding metadata attribute can comprise 'Acquisition date' as attribute tag and the exact date as attribute value. It cannot be checked based on the medical image whether the attribute value is correct. Furthermore, the exact date of acquisition cannot be determined based on the medical image by applying the method described above if the attribute value is empty. Hence, this example metadata attribute is not suited to be autofilled and/or corrected by applying the method described above. Hence, based on the attribute tags, only such metadata attributes can be determined out of the plurality of metadata attributes to be potentially the at least one first metadata attribute whose attribute values can be autofilled and/or corrected by applying the method described above based on the medical image. With other words, the at least one first metadata attribute is determined in dependence of the corresponding attribute tag.

Figure 8:
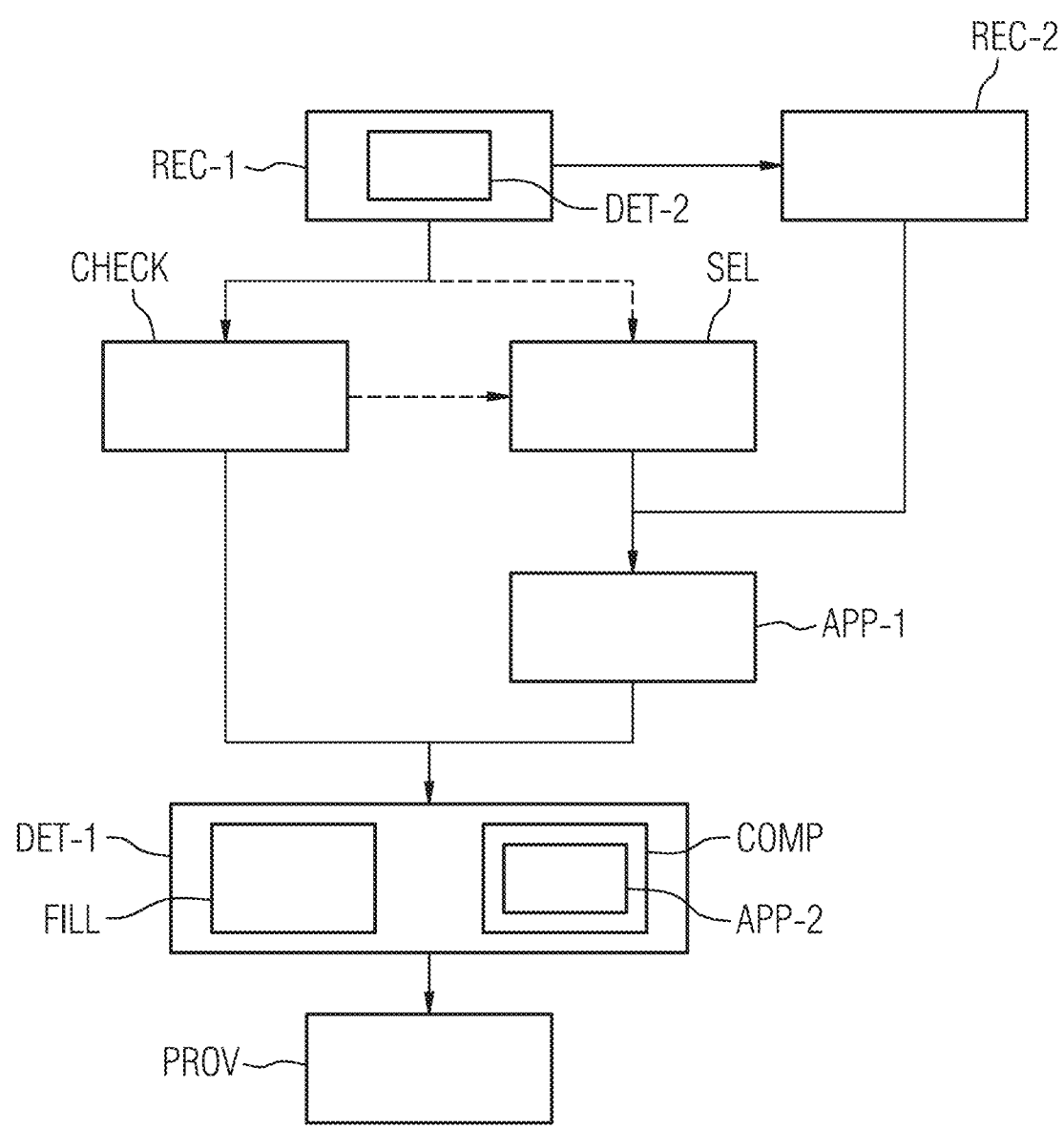

FIG. 8 displays a schematic flow chart of an eighth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5. The step of selecting SEL the first trained function can be performed according to FIG. 6. The step of determining DET-2 the at least one first metadata attribute is performed according to FIG. 7.

In this embodiment, the method comprises a step of receiving REC-2 at least one second metadata attribute out of a plurality of metadata attributes. The plurality of metadata attributes corresponds to the plurality of metadata attributes as described above. In particular, the plurality of metadata attributes comprises the at least one first metadata attribute and the at least one second metadata attribute. The at least one second metadata attribute is related to the at least one first metadata attribute. With other words, the at least one first metadata attribute and the at least one second metadata attribute relate to the same field respectively context with respect to the medical image. For example, both metadata attributes can relate to an information about what is depicted in the medical image. For example, the at least one second metadata attribute can provide an information about the examined body part of the examination object. With other words, the at least one second metadata attribute can comprise the attribute tag 'Body part examined' and for example the attribute value 'Thorax'. In this case, the at least one first metadata attribute can provide an information about the organ depicted by the medical image. For example, the at least one first metadata attribute can comprise the attribute tag 'Organ' and the provisional attribute value 'heart'. Alternatively, the provisional attribute value can be empty. Hence, the at least one second metadata attribute can be a more general information in the same field as the at least one first metadata attribute. With other words, the at least one second metadata attribute provides some pre-information which can be relevant for determining the image-based attribute value. For example, the image-based attribute value cannot be 'brain' in the example from above, if the thorax of the examination object is imaged in the medical image. Hence, the at least one second metadata attribute can be used to accelerate and/or control the step of determining DET-1 the image-based attribute value of the at least one first metadata attribute by providing some pre-information. Alternatively or additionally, the at least one second metadata attribute can be used for a consistency check whether the image-based attribute value makes sense considering the at least one second metadata attribute.

The first trained function is also applied to the at least one second metadata attribute in the step of applying APP-1 the first trained function. Hence, as described above, the image-based attribute value of the at least one first metadata attribute can be determined considering the at least one second metadata attribute.

Alternatively or additionally, the step of selecting SEL the first trained function can depend on the at least one second metadata attribute. As described above, the first trained functions of the plurality of first trained functions can be specialized for a specific field. Based on the attribute tag and attribute value of the at least one second metadata attribute and optionally on the attribute tag of the at least one first metadata attribute, the best suited first trained function can be selected. According to the example of above, a trained function suited for determining the organs in a thorax can be selected based on the at least one second metadata attribute and the attribute tag of the at least one first metadata attribute.

In particular, the method can comprise a step of determining the at least one second metadata attribute based on the attribute tag of the at least one first metadata attribute. Therein, at least one metadata attribute, which is in the same field as the at least one first metadata attribute, is determined out of the plurality of metadata attributes to be the at least one second metadata attribute. Alternatively, the related metadata attributes can be pre-defined. With other words, relations between the metadata attributes of the plurality of metadata attributes can be defined in advance. Related metadata attributes can be received together.

Figure 9:
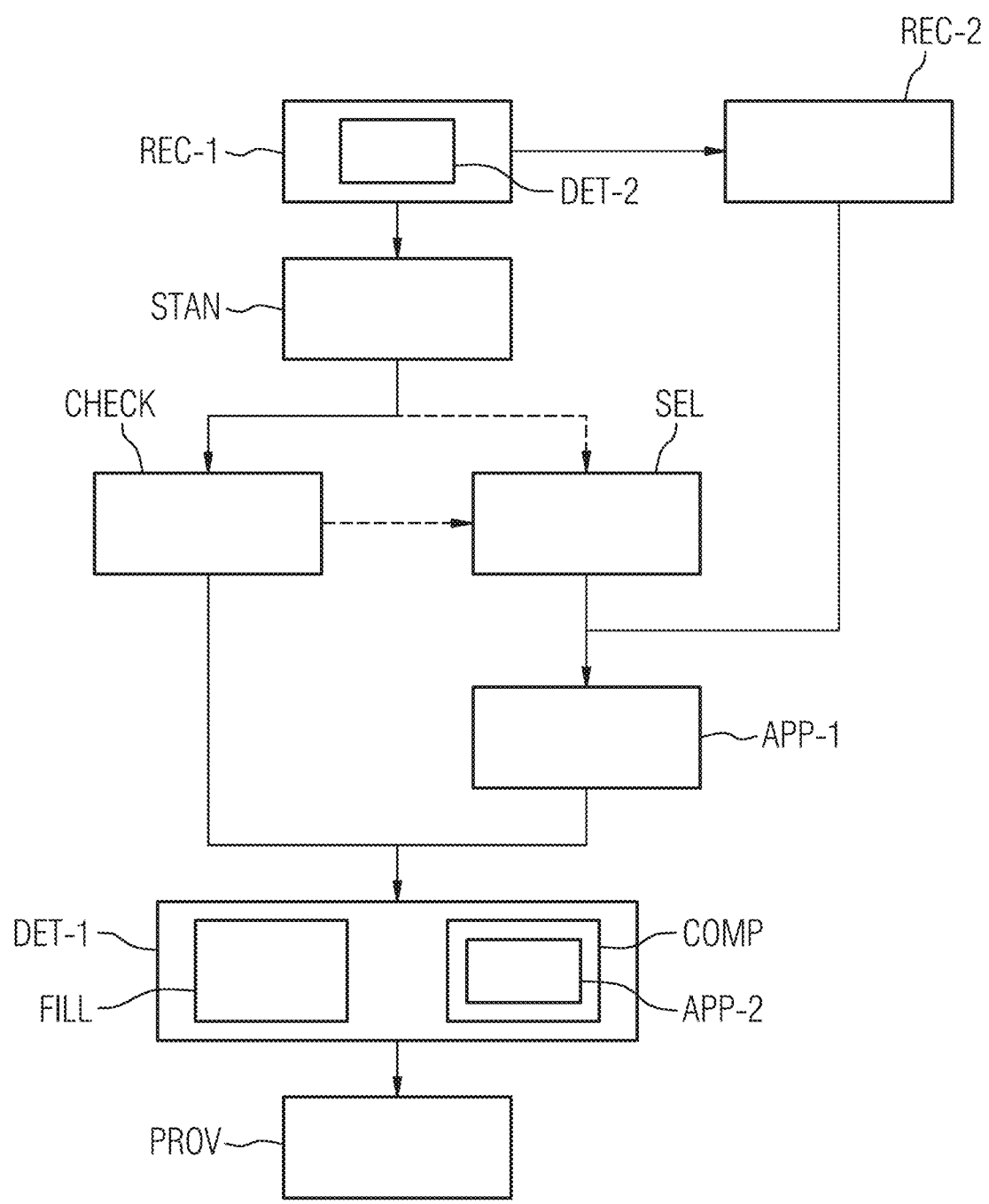

FIG. 9 displays a schematic flow chart of a ninth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5. The step of selecting SEL the first trained function can be performed according to FIG. 6. The step of determining DET-2 the at least one first metadata attribute is performed according to FIG. 7. The step of receiving REC-2 the at least one second metadata attribute is performed according to FIG. 8.

The provisional attribute value of the at least one first metadata attribute comprises a free-text attribute value. The free-text attribute value can for example be filled in by a medical doctor and/or a medical assistant. The free-text attribute value is in particular not restricted by any rules. The free-text attribute value can for example comprise an abbreviation and/or a not-standardized expression and/or an acronym. The free-text attribute values can differ between the persons who filled in the free-text attribute value. With other words, the free-text attribute can be individual. The free-text attribute value can for example be 'Thx p.a. LR ER' or 'Chest AP Port'.

In a step of standardizing STAN the free-text attribute value, the free-text attribute value is standardized by applying a third trained function to the at least one first metadata attribute. Therein the free-text attribute value is replaced by the standardized attribute value in the provisional attribute value of the at least one first metadata attribute. With other words, the provisional attribute value comprises the standardized attribute value after applying the third trained function. By applying the third trained function the free-text attribute value is standardized based on a standard ontology like RadLex or SNOMED-CT and/or based on a privately defined dictionary. The privately defined dictionary can be designed as described above. The third trained function can be trained and designed as described above. According to the examples of FIG. 8, the standardized attribute values can be 'Thorax Posterior Anterior Left Right Emergency Room' and 'Chest anterior posterior portable'.

The provisional attribute value comprising the standardized attribute value can be used in the step of determining DET-1 the final attribute value.

Figure 10:
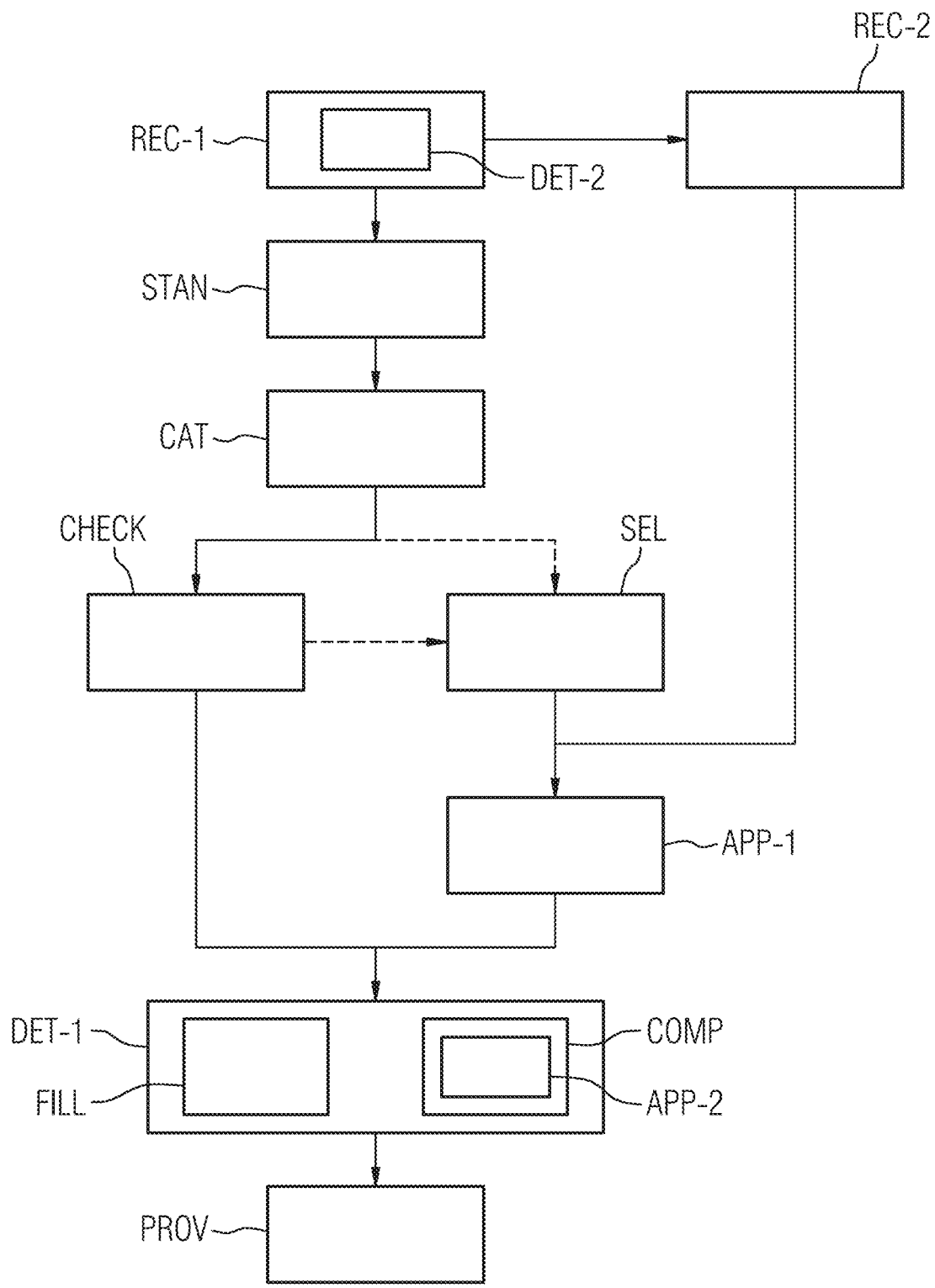

FIG. 10 displays a schematic flow chart of a tenth embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5. The step of selecting SEL the first trained function can be performed according to FIG. 6. The step of determining DET-2 the at least one first metadata attribute is performed according to FIG. 7. The step of receiving REC-2 the at least one second metadata attribute is performed according to FIG. 8. The step of standardizing STAN the free-text attribute value is performed according to FIG. 9.

In a step of categorizing CAT the standardized attribute value, the categorized standardized attribute value is determined by applying a fourth trained function. Therein the standardized attribute value is replaced by the categorized standardized attribute value in the provisional attribute value of the at least one first metadata attribute.

The fourth trained function can be designed as described above. By categorizing the standardized attribute value each expression of the standardized attribute value is categorized. According to the example of FIG. 9, the standardized attribute values can be categorized as following: [Thorax]→'Anatomy', [Posterior Anterior]→'View Position', [Left Right]→'Patient Orientation', [Emergency Room]→'Location', and [Chest]→'Anatomy', [Anterior Posterior]→'View Position', [Portable]→'Modality'. Therein 'Anatomy', 'View Position', 'Patient Orientation', 'Location, 'Modality' are categories for categorizing the expression comprised by the standardized attribute values. There are more categories possible for categorizing the standardized attribute value.

The provisional attribute value comprising the categorized standardized attribute value can be used in the step of determining DET-1 the final attribute value.

Figure 11:
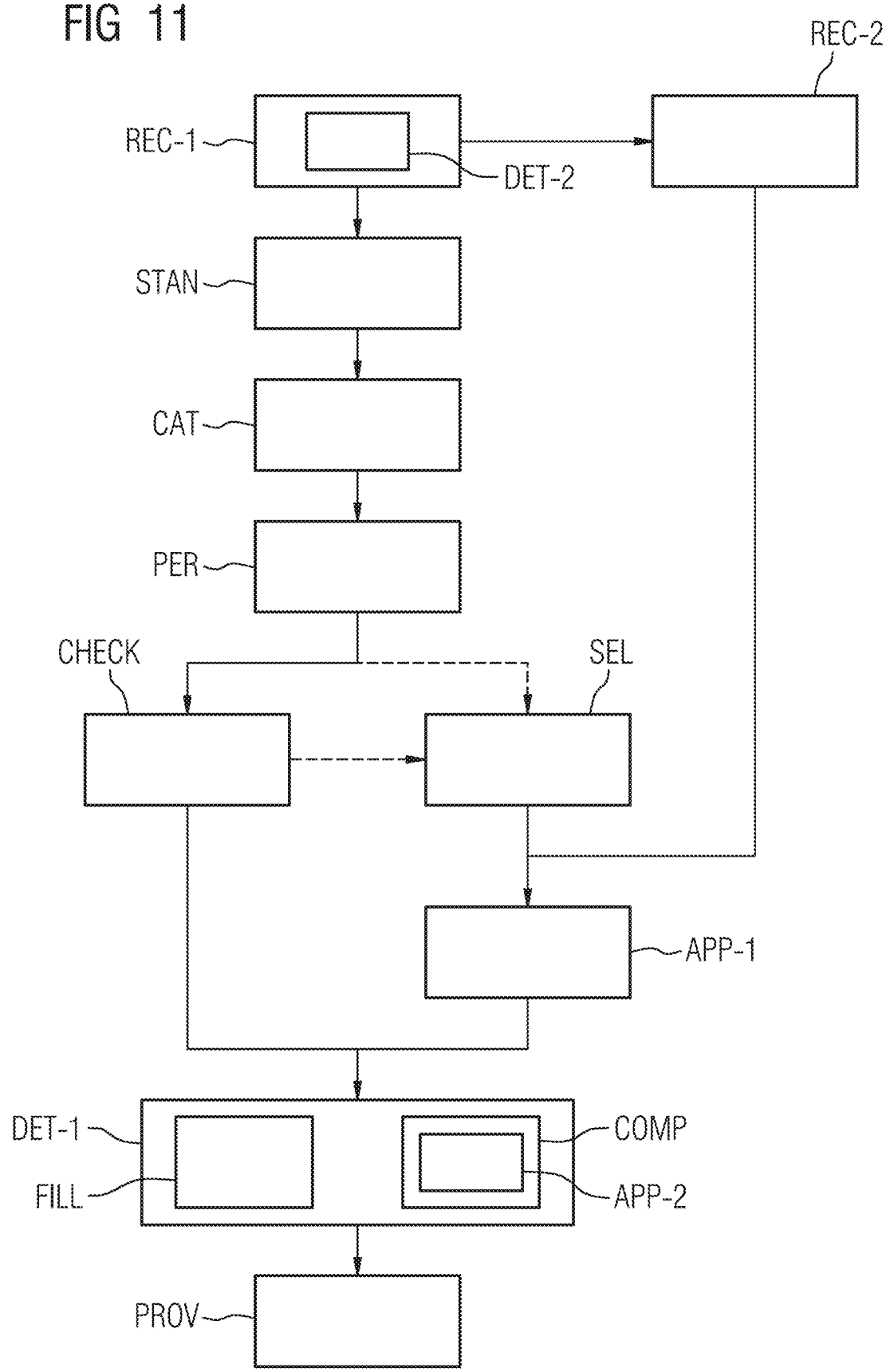

FIG. 11 displays a schematic flow chart of an eleventh embodiment of the method for providing at least one first metadata attribute associated with a medical image.

The steps of receiving REC-1 the medical image and the at least one first metadata attribute, of applying APP-1 the first trained function, of determining DET-1 the final attribute value and of providing PROV the at least one first metadata attribute are performed in the same manner as described according to FIG. 1. The step of checking CHECK whether the provisional attribute value is empty is performed according to FIG. 2. The step of filling FILL the final attribute value with the image-based attribute value is performed according to FIG. 3. The step of comparing COMP the provisional attribute value and the image-based attribute value is performed according to FIG. 4. The step of applying APP-2 the second trained function can be performed according to FIG. 5. The step of selecting SEL the first trained function can be performed according to FIG. 6. The step of determining DET-2 the at least one first metadata attribute is performed according to FIG. 7. The step of receiving REC-2 the at least one second metadata attribute is performed according to FIG. 8. The step of standardizing STAN the free-text attribute value is performed according to FIG. 9. The step of categorizing CAT the standardized attribute value can be performed according to FIG. 10.

In a step of performing PER a semantic matching of the categorized standardized attribute value the categorized standardized attribute value is matched with higher level terms by applying a fifth trained function. Therein the categorized standardized attribute value is replaced by the matched categorized standardized attribute value in the provisional attribute value of the at least one first metadata attribute.

The fifth trained function can be designed as described above. The higher-level terms are in particular in accordance with a standardized ontology like RadLex and/or SNOMED-CT and and/or with a privately defined dictionary as described above. In particular during the semantic matching, a concrete expression within the categorized standardized attribute value can be replaced by a more general one according to the standard ontology and/or privately defined dictionary. For the examples of FIGS. 9 and 10 the matched categorized standardized attribute values are 'Chest Posterior Anterior Left Right Emergency Room' and 'Chest Anterior Posterior Portable X-Ray'. For clarity reasons, the categories are omitted here. Hence, the expression 'Thorax' is replaced by the more general higher-level term 'Chest' and the expression 'Portable' is replaced by the higher-level term 'Portable X-Ray'.

The provisional attribute value comprising the matched categorized standardized attribute value can be used in the step of determining DET-1 the final attribute value.

Alternatively, the semantic matching can be performed on the standardized attribute value. With other words, the expressions within the standardized attribute value can be matched and the categorization can be omitted or performed afterwards. The standardized attribute value can then be replaced by the matched standardized attribute value in the provisional attribute value. The provisional attribute value comprising the matched standardized attribute value can be used in the step of determining DET-1 the final attribute value.

Figure 12:
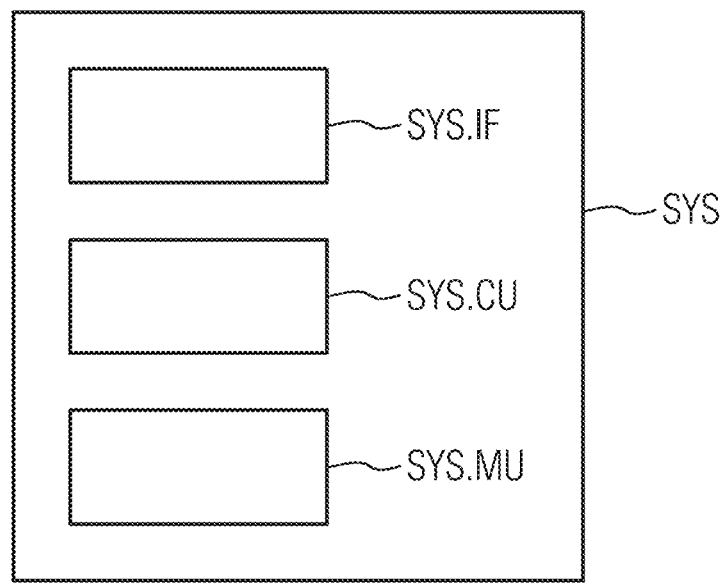
Figure 13:
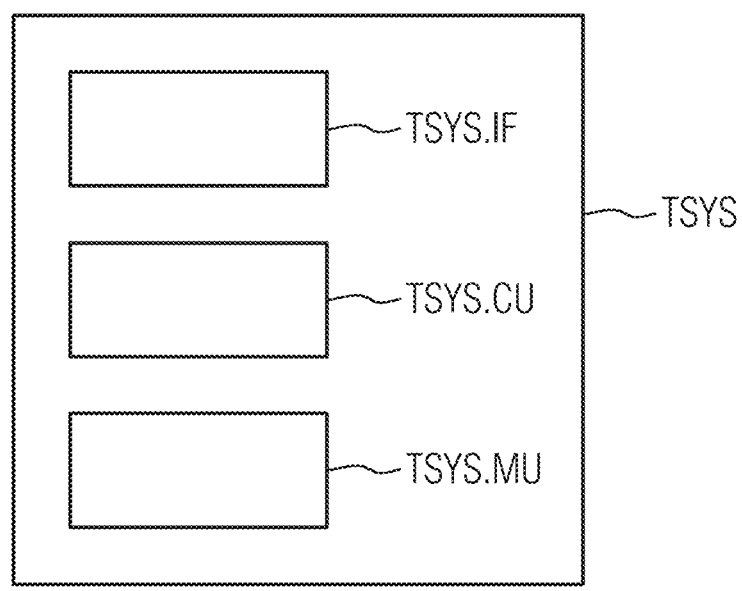

FIG. 12 displays a unifying system SYS, FIG. 13 displays a training system TSYS. The displayed unifying system SYS is configured to execute a method according to the invention for providing at least one first metadata attribute associated with a medical image. The training system TSYS shown is designed to carry out a method according to the invention for providing a first trained function. A training system for providing a second, third, fourth or fifth trained function can be configured accordingly. The unifying system SYS comprises an interface SYS.IF, a computation unit SYS.CU, and a memory unit SYS.MU. The training system TSYS comprises a training interface TSYS.IF, a training computational unit TSYS.CU, and a training memory unit TSYS.MU The unifying system SYS and/or the training system TSYS can in particular be a computer, a microcontroller or an integrated circuit. Alternatively, the unifying system SYS and/or the training system TSYS can be a real or a virtual network of computers (a technical term for a real network is "cluster", a technical term for a virtual network is "cloud"). The unifying system SYS and/or the training system TSYS can also be designed as virtual system that is executed on a computer, a real network of computers or a virtual network of computers (a technical term is "virtualization").

An interface SYS.IF and/or a training interface TSYS.IF can be a hardware or software interface (for example PCI bus, USB or Firewire). A computation unit SYS.CU and/or a training computation unit TSYS.CU can have hardware elements or software elements, for example a microprocessor or a so-called FPGA (acronym for "field programmable gate way"). A memory unit SYS.MU and/or a training memory unit TSYS.MU can be implemented as a non-permanent working memory (random access memory, RAM for short) or as a permanent mass storage device (hard disk, USB stick, SD card, solid state disk).

The interface SYS.IF and/or the training interface TSYS.IF can in particular comprise a plurality of sub-interfaces which carry out different steps of the respective method. In other words, the interface SYS.IF and/or the training interface TSYS.IF can also be understood as a plurality of interfaces SYS.IF and/or a plurality of training interfaces TSYS.IF. The computation unit SYS.CU and/or the training computation unit TSYS.CU can in particular comprise a plurality of sub-computing units which carry out different steps of the respective method. In other words, the computation unit SYS.CU and/or the training computation unit TSYS.CU can also be understood as a plurality of computation units SYS.CU and/or a plurality of training computation units TSYS.CU.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing at least one first metadata attribute associated with a medical image, the computer-implemented method comprising:
    receiving the medical image and the at least one first metadata attribute, the received at least one first metadata attribute including an attribute tag and a provisional attribute value;
    applying a first trained function to the medical image to determine an image-based attribute value;
    checking whether the provisional attribute value is empty;
    determining a final attribute value based on the provisional attribute value, the image-based attribute value, and a result of the checking; and
    providing the at least one first metadata attribute, the provided at least one first metadata attribute including the attribute tag and the final attribute value.

2. The computer-implemented method of claim 1, wherein the determining of the final attribute value includes,
    filling the final attribute value with the image-based attribute value upon the provisional attribute value being empty.

3. The computer-implemented method of claim 1, wherein the determining of the final attribute value includes,
    comparing the provisional attribute value and the image-based attribute value upon the provisional attribute value not being empty, and wherein
    the final attribute value is determined based on the comparing.

4. The computer-implemented method of claim 3, wherein the comparing of the provisional attribute value and the image-based attribute value comprises:
    applying a second trained function to the provisional attribute value and the image-based attribute value to determine the final attribute value.

5. The computer-implemented method of claim 4, wherein the first trained function includes the second trained function.

6. The computer-implemented method of claim 1, further comprising:
    selecting the first trained function from a plurality of first trained functions based on at least one of the result of the checking or the attribute tag.

7. The computer-implemented method of claim 1, wherein a plurality of metadata attributes are associated with the medical image, wherein each metadata attribute of the plurality of metadata attributes includes an attribute tag and an attribute value, wherein the at least one first metadata attribute is a metadata attribute of from among the plurality of metadata attributes, and wherein the method further includes determining the at least one first metadata attribute out of the plurality of metadata attributes, based on at least one of an application configured to process the medical image or the attribute tags.

8. The computer-implemented method of claim 1,
wherein a plurality of metadata attributes are associated with the medical image,
wherein the at least one first metadata attribute is a metadata attribute of from among the plurality of metadata attributes,
wherein the method further includes receiving at least one second metadata attribute from among the plurality of metadata attributes,
wherein the at least one second metadata attribute is related to the at least one first metadata attribute, and
wherein first trained function is also applied to the at least one second metadata attribute in the applying of the first trained function.

9. The computer-implemented method of claim 1,
wherein the provisional attribute value includes a free-text attribute value,
wherein the method further includes standardizing the free-text attribute value by applying a third trained function to the at least one first metadata attribute, and
wherein the free-text attribute value is replaced by the standardized attribute value in the provisional attribute value of the at least one first metadata attribute.

10. The computer-implemented method of claim 9, further comprising:
categorizing the standardized attribute value by applying a fourth trained function to the at least one first metadata attribute, and
wherein the standardized attribute value is replaced by the categorized standardized attribute value in the provisional attribute value of the at least one first metadata attribute.

11. The computer-implemented method of claim 10, further comprising:
performing a semantic matching of the categorized standardized attribute value with higher-level terms by applying a fifth trained function to the at least one metadata attribute, and wherein
the categorized standardized attribute value is replaced by the matched categorized standardized attribute value in the provisional attribute value of the at least one first metadata attribute.

12. The computer-implemented method of claim 2, wherein the determining of the final attribute value includes,
comparing the provisional attribute value and the image-based attribute value upon the provisional attribute value not being empty, and wherein
the final attribute value is determined based on the comparing.

13. The computer-implemented method of claim 12, wherein the comparing of the provisional attribute value and the image-based attribute value comprises:
applying a second trained function to the provisional attribute value and the image-based attribute value to determine the final attribute value.

14. The computer-implemented method of claim 13, wherein the first trained function includes the second trained function.

15. The computer-implemented method of claim 2, further comprising:
selecting the first trained function from a plurality of first trained functions based on at least one of the result of the checking or the attribute tag.

16. The computer-implemented method of claim 2, further comprising:
selecting the first trained function from a plurality of first trained functions based on the at least one second metadata attribute.

17. A unifying system for providing at least one metadata attribute associated with a medical image, the unifying system comprising:
an interface configured to
receive the medical image and the at least one metadata attribute, the received at least one metadata attribute including an attribute tag and a provisional attribute value, and
provide the at least one metadata attribute, the provided at least one metadata attribute including the attribute tag and a final attribute value; and at least one processor configured to
apply a first trained function to the medical image to determine an image-based attribute value,
check whether the provisional attribute value is empty, and
determine the final attribute value based on the provisional attribute value, the image-based attribute value, and a result of the check.

18. A non-transitory computer program product storing program elements that are loaded into a memory of a unifying system including at least one processor, the program elements inducing the unifying system to execute the computer-implemented method of claim 1, when the program elements are executed by the at least one processor-unifying system.

19. A non-transitory computer-readable storage medium storing program elements that, when executed by at least one processor at a unifying system, cause the unifying system to perform the computer-implemented method of claim 1.

20. A computer-implemented method for providing at least one first metadata attribute associated with a medical image, the computer-implemented method comprising:
receiving the medical image and the at least one first metadata attribute, the received at least one first metadata attribute including an attribute tag and a provisional attribute value;
applying a first trained function to the medical image to determine an image-based attribute value;
determining a final attribute value based on the provisional attribute value and the image-based attribute value; and
providing the at least one first metadata attribute, the provided at least one first metadata attribute including the attribute tag and the final attribute value; wherein
the provisional attribute value includes a free-text attribute value,
the method further includes standardizing the free-text attribute value by applying a second trained function to the received at least one first metadata attribute, and the free-text attribute value is replaced by the standardized attribute value in the provisional attribute value of the received at least one first metadata attribute.

* * * * *